US011339332B2

(12) United States Patent
Shaikh et al.

(10) Patent No.: US 11,339,332 B2
(45) Date of Patent: May 24, 2022

(54) SYSTEMS AND PROCESSES INTEGRATING FLUIDIZED CATALYTIC CRACKING WITH METATHESIS FOR PRODUCING OLEFINS

(71) Applicant: Saudi Arabian Oil Company, Dhahran (SA)

(72) Inventors: Sohel K. Shaikh, Dhahran (SA); Raed H. Abudawoud, Khobar (SA); Zhonglin Zhang, Dhahran (SA); Munir D. Khokhar, Dhahran (SA); Furqan Aljumah, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/775,677

(22) Filed: Jan. 29, 2020

(65) Prior Publication Data

US 2021/0238485 A1    Aug. 5, 2021

(51) Int. Cl.
*C07C 4/06*  (2006.01)
*C07C 6/04*  (2006.01)
(Continued)

(52) U.S. Cl.
CPC ............... *C10G 11/18* (2013.01); *C07C 4/06* (2013.01); *C07C 6/04* (2013.01); *C07C 41/06* (2013.01);
(Continued)

(58) Field of Classification Search
None
See application file for complete search history.

(56) References Cited

U.S. PATENT DOCUMENTS 3,442,821 A    5/1969  Lee
3,546,313 A    12/1970 Banks
(Continued)

FOREIGN PATENT DOCUMENTS

CN    100448820 C    1/2009
CN    101514135 A    8/2009
(Continued)

OTHER PUBLICATIONS

Arudra et al., "Silicalite-1 as Efficient Catalyst for Production of Propene from 1-Butene", ACS Catalysis, 2014, 4205-4212, 4, American Chemical Society.
(Continued)

*Primary Examiner* — Philip Y Louie
(74) *Attorney, Agent, or Firm* — Dinsmore & Shohl, LLP

(57) ABSTRACT

Processes for producing olefins include introducing a hydrocarbon feed to a high-severity fluidized catalytic cracking system, contacting the hydrocarbon feed with a cracking catalyst under high-severity conditions in the high-severity fluidized catalytic cracking system to produce a cracking reaction effluent comprising butene, and passing at least a portion of the cracking reaction effluent, which includes at least butene, to a metathesis system. The processes further include contacting the portion of the cracking reaction effluent with a metathesis catalyst in the metathesis system, which causes at least a portion of the butene in the cracking C4 effluent to undergo a metathesis reaction to produce a metathesis reaction effluent comprising at least one of ethylene, propene, or both. The processes may further include separating a metathesis C5+ effluent from the metathesis reaction effluent and passing the metathesis C5+ effluent back to the high-severity fluidized catalytic cracking unit.

16 Claims, 6 Drawing Sheets

(51) Int. Cl.
  *C07C 41/06* (2006.01)
  *C10G 11/18* (2006.01)
  *C07C 43/04* (2006.01)
  *C10G 29/22* (2006.01)
  *C10G 57/00* (2006.01)

(52) U.S. Cl.
  CPC ............ *C07C 43/046* (2013.01); *C10G 29/22* (2013.01); *C10G 57/00* (2013.01); *C10G 2300/1096* (2013.01); *C10G 2300/4006* (2013.01); *C10G 2300/4081* (2013.01); *C10G 2400/20* (2013.01)

(56) References Cited

U.S. PATENT DOCUMENTS

| | | |
|---|---|---|
| 3,586,731 A | 6/1971 | Heckelsberg |
| 3,702,886 A | 11/1972 | Argauer et al. |
| 3,728,415 A | 4/1973 | Arganbright |
| 4,024,201 A | 5/1977 | Takahashi |
| 4,071,471 A | 1/1978 | Banks et al. |
| 4,575,575 A | 3/1986 | Drake et al. |
| 4,609,769 A | 9/1986 | Kukes et al. |
| 5,026,935 A | 6/1991 | Leyshon et al. |
| 5,026,936 A | 6/1991 | Leyshon et al. |
| 5,191,131 A | 3/1993 | Takahata et al. |
| 5,439,859 A | 8/1995 | Durante et al. |
| 5,523,502 A | 6/1996 | Rubin |
| 5,877,365 A | 3/1999 | Chodorge et al. |
| 6,159,433 A | 12/2000 | Chodorge et al. |
| 6,207,115 B1 | 3/2001 | Chodorge et al. |
| 6,215,062 B1 | 4/2001 | Kimber |
| 6,538,168 B1 | 3/2003 | Schwab et al. |
| 6,580,009 B2 | 6/2003 | Schwab et al. |
| 6,586,649 B1 | 7/2003 | Botha et al. |
| 6,646,172 B1 | 11/2003 | Schwab et al. |
| 6,777,582 B2 | 8/2004 | Gartside et al. |
| 6,977,321 B1 | 12/2005 | Dath et al. |
| 7,214,841 B2 | 5/2007 | Gartside et al. |
| 7,754,647 B2 | 7/2010 | Schubert et al. |
| 7,754,934 B2 | 7/2010 | Tsunoda et al. |
| 7,977,522 B2 | 7/2011 | Takai et al. |
| 8,299,313 B2 | 10/2012 | Takai et al. |
| 8,324,440 B2 | 12/2012 | Popp et al. |
| 8,362,308 B2 | 1/2013 | Stephan et al. |
| 8,440,874 B2 | 5/2013 | Ramachandran et al. |
| 8,586,813 B2 | 11/2013 | Ramachandran et al. |
| 8,722,568 B2 | 5/2014 | Popp et al. |
| 9,834,497 B2 | 12/2017 | Shaikh et al. |
| 9,884,794 B2 | 2/2018 | Al-Khattaf et al. |
| 2003/0176754 A1 | 9/2003 | Gartside et al. |
| 2004/0254411 A1 | 12/2004 | Steinbrenner et al. |
| 2005/0014981 A1 | 1/2005 | Gartside et al. |
| 2005/0124839 A1 | 6/2005 | Gartside et al. |
| 2006/0047176 A1* | 3/2006 | Gartside ................ C07C 7/144 585/643 |
| 2006/0293548 A1 | 12/2006 | Spamer et al. |
| 2007/0038010 A1 | 2/2007 | Xie et al. |
| 2007/0225478 A1 | 9/2007 | Querci et al. |
| 2008/0033223 A1* | 2/2008 | Sigl ............................ C07C 6/04 585/324 |
| 2008/0171655 A1 | 7/2008 | Creyghton et al. |
| 2010/0041930 A1 | 2/2010 | Gartside et al. |
| 2010/0168487 A1 | 7/2010 | Sawyer et al. |
| 2010/0234542 A1 | 9/2010 | Blackborow et al. |
| 2011/0021858 A1 | 1/2011 | Ramachandran et al. |
| 2011/0152595 A1 | 6/2011 | Takai et al. |
| 2011/0196185 A1 | 8/2011 | Krawczyk et al. |
| 2012/0108864 A1 | 5/2012 | Gartside et al. |
| 2012/0264990 A1 | 10/2012 | Nicholas et al. |
| 2012/0283090 A1 | 11/2012 | Popp et al. |
| 2012/0289617 A1 | 11/2012 | Wang et al. |
| 2013/0085311 A1 | 4/2013 | Youn et al. |
| 2013/0165701 A1 | 6/2013 | Zhou et al. |
| 2013/0245348 A1 | 9/2013 | Vermeiren et al. |
| 2013/0303806 A1* | 11/2013 | Winterberg ............. C07C 1/20 203/99 |
| 2014/0148629 A1 | 5/2014 | van Hal et al. |
| 2015/0141720 A1 | 5/2015 | Ramachandran et al. |
| 2015/0141721 A1 | 5/2015 | Choi et al. |
| 2015/0251968 A1* | 9/2015 | Brianti .................... C07C 41/06 585/639 |
| 2016/0130197 A1 | 5/2016 | Al-Khattaf et al. |
| 2016/0237006 A1 | 8/2016 | Stoyanova et al. |
| 2017/0001925 A1 | 1/2017 | Abudawoud et al. |
| 2017/0001926 A1 | 1/2017 | Shaikh et al. |
| 2017/0001927 A1 | 1/2017 | Al-Khattaf et al. |
| 2017/0001928 A1 | 1/2017 | Shaikh et al. |
| 2017/0253540 A1 | 9/2017 | Hofel et al. |
| 2018/0057425 A1 | 3/2018 | Shaikh et al. |
| 2018/0142167 A1 | 5/2018 | Al-Ghamdi et al. |
| 2018/0208524 A1 | 7/2018 | Alshafei et al. |
| 2018/0208526 A1 | 7/2018 | Alshafei et al. |
| 2018/0208527 A1 | 7/2018 | Khokhar et al. |
| 2018/0230071 A1 | 8/2018 | Bonduelle et al. |
| 2019/0367432 A1 | 12/2019 | Al-Majnouni et al. |

FOREIGN PATENT DOCUMENTS

| | | |
|---|---|---|
| CN | 101531558 A | 9/2009 |
| CN | 102325742 A | 1/2012 |
| CN | 104370676 A | 2/2015 |
| DE | 10013253 A1 | 9/2001 |
| EP | 304515 B1 | 12/1991 |
| EP | 920911 A1 | 6/1999 |
| EP | 2151424 A1 | 2/2010 |
| GB | 1205677 A | 9/1970 |
| JP | 2003500190 A | 1/2003 |
| JP | 2012500304 A | 1/2012 |
| NL | 8403050 A | 5/1986 |
| RU | 2370314 C1 | 10/2009 |
| WO | 9929805 A1 | 6/1999 |
| WO | 0071255 A1 | 11/2000 |
| WO | 2006089957 A1 | 8/2006 |
| WO | 2008136280 A1 | 11/2008 |
| WO | 2009015118 A2 | 1/2009 |
| WO | 2009117128 A1 | 9/2009 |
| WO | 2010019595 A2 | 2/2010 |
| WO | 2011136983 A1 | 11/2011 |
| WO | 2015055594 A1 | 4/2015 |
| WO | 2017003812 A1 | 1/2017 |
| WO | 2017003817 A1 | 1/2017 |
| WO | 2017003821 A1 | 1/2017 |
| WO | 2018088815 A1 | 5/2018 |

OTHER PUBLICATIONS

Awayssa et al., "Modified HZSM-5 as FCC Additive for Enhancing Light Olefins Yield from Catalytic Cracking of VGO", Applied Catalysis A: General, 2014, 172-183, 477.

Balcar, et al., "Mesoporous molecular sieves as advanced supports for olefin metathesis catalysts", Coordination Chemistry Reviews 257, 2013, pp. 3107-3124, Czech Republic.

Barrett et al., "The Determination of Pore Volume and Area Distributions in Porous Substances. I. Computations from Nitrogen Isotherms", J. Am. Chem. Soc., 1951, 373-380, 73(1).

Beck et al., "A New Family of Mesoporous Molecular Sieves Prepared with Liquid Crystal Templates", J. Am. Chem. Soc., 1992, 10834-10843, 114, American Chemical Society.

Bhuiyan et al., "Kinetics Modelling of 2-Butene Metathesis Over Tungsten Oxide Containing Mesoporous Silica Catalyst", The Canadian Journal of Chemical Engineering, 2014, 1271-1282. 92.

Bhuiyan et al., "Metathesis of 2-Butene to Propylene over W-Mesoporous Molecular Sieves: A Comparative Study Between Tungsten Containing MCM-41 and SBA-15", Applied Catalysis A: General, 2013, 224-234, 467, Elsevier B.V.

Bin Hu, et al., "Highly Active Doped Mesoporous KIT-6 Catalysts for Metathesis of 1-Butene and Ethene to Propene: The Influence of Neighboring Environment of W Species", The Journal of Physical Chemistry, ACS Publication, 2013 American Chemical Society, pp. 26385-26395, USA.

(56) References Cited

OTHER PUBLICATIONS

Daniell et al., "Enhanced Surface Acidity in Mixed Alumina-Silicas: A Low-Temperature" FTIR Study:, 2000, 196, 247-260, Elsevier.
Do et al., "Zeolite Nanoclusters Coated onto the Mesopore Walls of SBA-15", J. Am. Chem. Soc., 2004, 14324-14325, 126, American Chemical Society.
International Search Report and Written Opinion dated Nov. 11, 2016 pertaining to International Application No. PCT/US2016/039025.
International Search Report and Written Opinion dated Sep. 14, 2016 pertaining to International Application No. PCT/US2016/039012.
International Search Report and Written Opinion dated Sep. 27, 2016 pertaining to International Application No. PCT/US2016/0038967.
International Search Report and Written Opinion dated Sep. 14, 2016 pertaining to International Application No. PCT/US2016/039013.
Jermy et al., "Utilization of ZSM-5/MCM-41 Composite as FCC Catalyst Additive for Enhancing Propylene Yield from VGO Cracking", J. Porous Mater, 2012, 499-509, 19, Springer.
Kawai et al., "Metaethesis of Halogen-Containing Olefin Over Re2O7/Al2O3 Catalyst Promited with Alkylmetal as a Cocatalyst", Journal of Molecular Catalysis A: Chemical, 1998, 133, 51-59.
Kumar et al., "Performance of Nano Crystalline H-ZSM-5 As Additive in FCC Catalyst: A Review", International Journal of Research in Engineering and Tehnology, May 2014, vol. 3, pp. 481-485.
Lwin et al., "Olefin Metathesis by Supported Metal Oxide Catalysts", ACS Catalysis, 2014, 2505-2520, 4, American Chemical Society.
Office Action pertaining to U.S. Appl. No. 15/190,950 dated Sep. 27, 2017.
Office Action pertaining to U.S. Appl. No. 15/190,964 dated Nov. 2, 2017.
Quignard et al., "Aryloxide Ligands in Metathesis of Olefins and Olefinic Esters: Catalytic Behaviour ofW(OAr)2CI4 by SnMe4, Sn(n-Bu)4, Pb(n-Bu)4, MgNp2: synthesis of W(OAr)2CI2(CHCMe3)(OR2) and W(OAr)2CI(CHCMe3)(CH2CMe3)(OR2)", Journal of Molecular Catalysis, 1986, 36, 13-29.
Ruihua Gao, et al., "High-activity, single-site mesoporous WO3-MCF materials for the catalytic epoxidation of cycloocta-1,5-diene with aqueous hydrogen peroxide", Journal of Catalysis, 256, 2008, pp. 259-267, China.
Wang et al., "Synthesis and Structure of Silicalite-1/SBA-15 Composites Prepared by Carbon Templating and Crystallization", Journal of Materials Chemistry, 2007,4265-4273,17, The Royal Society of Chemistry 2007.
Wang et al., "Effect of Support Nature on WO3/SiO2 Structure and Butene-1 Metathesis", Applied Catalysis A: General, 2003, 25-37, 250, Elsevier B.V.
Zhao et al., "Effect of Tungsten Oxide Loading on Metathesis Activity of Ethene and 2-Butene Over WO3/SiO2 Catalysts" Transition Met Chem, 2009, 621-27, 34, Springer.
International Preliminary Report on Patentability dated Jan. 11, 2018—PCT/US2016/039012.
International Preliminary Report on Patentability dated Jan. 2, 2018—PCT/US2016/039012.
Non-Final Office Action pertaing to U.S. Appl. No. 15/398,196 dated Jan. 9, 2018.
Puriwat, et al., "Elucidation of the basicity dependence of 1-butene isomerization on MgO/Mg(OH)s catalysts", Catalysis Communications, 2010, pp. 80-85.
International Search Report and Written opinion dated Mar. 28, 2018, pertaining to International Application No. PCT/US2018/013945, filed Jan. 17, 2018, 9 pages.
U.S. Office Action dated Apr. 20, 2018 pertaining to U.S. Appl. No. 15/859,794, filed Jan. 2, 2018.
International Search Report and Written Opinion dated Apr. 24, 2018 pertaining to International Application No. PCT/US2018/014131, filed Jan. 18, 2018.
Notice of Allowance dated Apr. 24, 2018 pertaining to U.S. Appl. No. 15/190,964, filed Jun. 23, 2016.
Election/Restriction Requirement dated May 21, 2018, pertaining to U.S. Appl. No. 15/866,772, filed Jan. 10, 2018.
Korean Office Action pertaining to Korea Application No. 10-2018-7003238 dated May 14, 2018 (English Translation).
Office Action pertaining to U.S. Appl. No. 15/866,800 dated Jun. 29, 2018.
Office Action pertaining to U.S. Appl. No. 15/190,981 dated Apr. 4, 2017.
Office Action pertaining to U.S. Appl. No. 15/866,772 dated Aug. 28, 2018.
Harmse et al., "On the Product Formation in 1-Butene Methathesis over Supported Tungsten Catalysts", Catal. Lett, vol. 137, pp. 123-131, Apr. 2010.
Shaikh et al., "Self-Methathesis of Butenes to Propylene", Catalysis in Petroleum Refining & Petrochemicals, pp. 1-6, Dec. 7-8, 2015.
Debecker et al., "Preparation of Mo03/si02-Al2O3 methathesis catalysts via wet impregnation with different Mo precursors", Journal of Molecular Catalysis A: Chemical, 340, pp. 65-76, 2011.
Wu et al., "Investigation on acidity of zeolites bound with silica and alumina", Studies in Surface Science and Catalysis, 143, pp. 217-225, 2002.
Hu et al., "Highly active doped mesoporous KIT-6 catalysts for mathesis of 1-butene and ethene to propene: The influence of neiboring environment of W. species", Journal of Physical Chemistry, vol. 117, pp. 26385-26395, 2013.
Examination Report pertaining to GCC Application No. 2016/31672 dated Sep. 13, 2018.
Office Action dated Jan. 31, 2019 pertaining to U.S. Appl. No. 15/866,800, filed Jan. 10, 2018 (34 pg).
Notice of Allowance dated Mar. 5, 2019 pertaining to U.S. Appl. No. 15/866,772, filed Jan. 10, 2018.
Office Action dated Apr. 5, 2019 pertaining to U.S. Appl. No. 15/873,421, filed Jan. 17, 2018, 49 pgs.
Office Action dated May 2, 2019 pertaining to U.S. Appl. No. 15/859,794, filed Jan. 2, 2018, 30 pgs.
Office Action dated May 2, 2019 pertaining to U.S. Appl. No. 16/156,634, filed Oct. 10, 2018, 32 pgs.
Office Action dated Apr. 29, 2019 pertaining to U.S. Appl. No. 16/039,983, filed Jul. 19, 2018, 36 pgs.
Notice of Allowance and Fee(s) Due dated Oct. 19, 2020 pertaining to U.S. Appl. No. 15/866,800, filed Jan. 10, 2018, 27 pgs.
Notice of Allowance and Fee(s) Due dated Apr. 19, 2021 pertaining to U.S. Appl. No. 16/522,142, filed Jul. 25, 2019, 45 pgs.
Notice of Allowance and Fee(s) Due dated Apr. 21, 2021 pertaining to U.S. Appl. No. 16/156,634, filed Oct. 10, 2018, 47 pgs.
Yuan Guimei et al., Machine translation of CN 104370676, Feb. 2015.
Notice of Allowance and Fee(s) Due dated May 15, 2019 pertaining to U.S. Appl. No. 16/156,616, filed Oct. 10, 2018, 35 pgs.
U.S. Office Action dated Jun. 14, 2019 pertaining to U.S. Appl. No. 15/866,800, filed Jan. 10, 2018, 38 pgs.
Office Action dated Jun. 18, 2019 pertianing to Korean Patent Application No. 10-2018-7003251.
Office Action dated Mar. 30, 2019 pertaining to Japanese Patent Application No. 2017-567370.
European Search Report for Application No. 19163840.2 dated Aug. 2, 2019.
Chinese Office Action for Application No. 201811179717.1 dated Jun. 13, 2019.
European Search Report for Application No. 16738274.6 dated Aug. 1, 2019.
Notice of Allowance and Fee(s) Due dated Aug. 29, 2019 pertaining to U.S. Appl. No. 15/859,794, filed Jan. 2, 2018, 22 pgs.
Notice of Allowance and Fee(s) Due dated Sep. 26, 2019 pertaining to U.S. Appl. No. 15/873,421, filed Jan. 17, 2018, 30 pgs.
Examination Report for Application No. GC 2018/34631 dated Aug. 22, 2019.

(56) References Cited

OTHER PUBLICATIONS

Decision of Rejection pertaining to Japanese Application No. 2017-567370 dated Sep. 4, 2019.
Notice of Allowance and Fee(s) due dated Oct. 18, 2019 pertaining to U.S. Appl. No. 16/039,983, filed Jul. 19, 2018, 29 pgs.
Machine translation claims of CN 102177223 A, Sep. 2011.
Machine translation description CN 102177223 A, Sep. 2011.
Office Action dated Nov. 20, 2019 pertaining to U.S. Appl. No. 16/156,634, filed Oct. 10, 2018, 37 pgs.
Office Action pertaining to U.S. Appl. No. 15/866,800 dated Jan. 13, 2020.
Office Action pertaining to U.S. Appl. No. 16/390,523 dated Jan. 17, 2020.
Bortnovsky et al., "Cracking of pentenes to C2-C4 light olefins over zeolites and zeotypes Role of topology and acid site strength and concentration", Applied Catalysis A: General 287, pp. 203-213, 2005.
Debecker et al., "Aerosol route to nanostructured WO3—SiO2—Al2O3 methathesis catalysts: Toward higer propene yield", Applied Catalysis A: General 470, pp. 458-466, 2014.
International Search Report and Written Opinion pertaining to Application No. PCT/US2019/054378 dated Jan. 13, 2020.
International Search Report and Written Opinion pertaining to Application No. PCT/US2019/054377 dated Jan. 13, 2020.
Korean Office Action pertaining to Korea Application No. 10-2019-7005618 dated Feb. 25, 2020 (English Translation).
International Search Report and Written Opinion dated Feb. 23, 2021 pertaining to International application No. PCT/US2020/058640 filed Nov. 3, 2020, 14 pgs.
Notice of Allowance and Fee(s) Due dated Nov. 23, 2020 pertaining to U.S. Appl. No. 16/156,616, filed Oct. 10, 2018, 29 pgs.
U.S. Office Action dated Mar. 2, 2021 pertaining to U.S. Appl. No. 16/712,280, filed Dec. 12, 2019, 34 pgs.
U.S. Office Action dated Aug. 21, 2020 pertaining to U.S. Appl. No. 16/712,280, filed Dec. 12, 2019, 67 pgs.
U.S. Office Action dated Sep. 15, 2020 pertaining to U.S. Appl. No. 16/156,634, filed Oct. 10, 2018, 38 pgs.
U.S. Office Action dated Sep. 16, 2020 pertaining to U.S. Appl. No. 16/522,142, filed Jul. 25, 2019, 72 pgs.
Office Action dated May 27, 2020 pertaining to U.S. Appl. No. 16/156,616, filed Oct. 10, 2018, 31 pgs.
Office Action dated Jul. 24, 2020 pertaining to U.S. Appl. No. 15/866,800, filed Jan. 10, 2018, 51 pgs.
Office Action dated Jul. 14, 2020 pertaining to U.S. Appl. No. 16/390,523, filed Apr. 22, 2019, 42 pgs.
Examination Report pertaining to GCC Application No. 2016/31673 dated Apr. 7, 2020.
Search Report and Written Opinion pertaining to Singapore Application No. 10201913486W dated Jul. 21, 2020.
Notice of Allowance and Fee(s) Due dated Dec. 10, 2020 pertaining to U.S. Appl. No. 16/390,523, filed Apr. 22, 2019, 22 pgs.
Notice of Allowance and Fee(s) Due dated Jul. 23, 2021 pertaining to U.S. Appl. No. 16/712,280, filed Dec. 12, 2019, 24 pages.
International Search Report and Written Opinion dated May 31, 2021 pertaining to International application No. PCT/US2020/060438 filed Nov. 13, 2020, 12 pages.
Office Action dated Jul. 6, 2021 pertaining to Chinese Patent Application No. 201880006954.X.
Office Action dated Jul. 2, 2021 pertaining to Chinese Patent Application No. 201880010205.4.
U.S. Office Action dated Oct. 22, 2021 pertaining to U.S. Appl. No. 16/830,759, filed Mar. 26, 2020, 89 pages.

\* cited by examiner

SYSTEMS AND PROCESSES INTEGRATING FLUIDIZED CATALYTIC CRACKING WITH METATHESIS FOR PRODUCING OLEFINS

TECHNICAL FIELD

Embodiments of the present disclosure generally relate to systems and processes for producing olefins from hydrocarbon feed compositions, in particular, systems and processes that include high-severity fluid catalytic cracking (HS-FCC) and metathesis for producing olefins.

BACKGROUND

Ethylene, propene, butene, butadiene, and aromatics compounds such as benzene, toluene and xylenes are basic intermediates for the petrochemical industry. These compounds are usually produced through thermal cracking (or steam pyrolysis) of petroleum gases and distillates such as naphtha, kerosene, or even gas oil. These compounds are also produced through a refinery fluidized catalytic cracking (FCC) process where classical heavy feedstocks such as gas oils or residues are converted. Typical FCC feedstocks range from hydrocracked bottoms to heavy feed fractions such as vacuum gas oil and atmospheric residue; however, these feedstocks are limited. The second most important source for propene production is currently refinery propene from FCC units.

The worldwide increasing demand for light olefins remains a major challenge for many integrated refineries. In particular, the production of some valuable light olefins such as ethylene, propene, and butene has attracted increased attention as pure olefin streams are considered the building blocks for polymer synthesis. The production of light olefins depends on several process variables, such as the feed type, operating conditions, and the type of catalyst. Despite the options available for producing a greater yield of propene and light olefins, intense research activity in this field is still being conducted. These options include the use of HS-FCC systems, developing more selective catalysts for the process, and enhancing the configuration of the process in favor of more advantageous reaction conditions and yields. The HS-FCC process is capable of producing yields of propene up to four times greater than the traditional fluid catalytic cracking unit and greater conversion levels for a range of petroleum steams.

SUMMARY

However, even under high-severity conditions, fluidized catalytic cracking units can produce substantial amounts of C4+ compounds, such as mixed butenes (1-butene, trans-2-butene, cis-2-butene, isobutene) butane, and isobutane, as well as pentene and other C5+ compounds. Production of these larger hydrocarbons, which may be of lesser value as chemical intermediates compared to propene and ethylene, may reduce the selectivity and yield of propene, ethylene, or both, from the fluidized catalytic cracking process. Additionally, typical feedstocks for the fluidized catalytic cracking process have included greater boiling feed compositions such as vacuum gas oils (VGO) and atmospheric residue feedstocks.

Accordingly, ongoing needs exist for processes and systems for producing olefins, such as propene and ethylene, from hydrocarbon feedstocks at greater selectivity and yield of propene, ethylene, or both, compare to commercially available fluidized catalytic cracking processes. Additionally, ongoing needs exist for processes and systems for producing olefins, such as propene and ethylene, from a broader spectrum of hydrocarbon feedstocks, such as feedstocks including naphtha streams or gas condensate streams. The processes and systems of the present disclosure include a high-severity fluidized catalytic cracking (HS-FCC) process integrated with a metathesis process downstream of the HS-FCC process. The HS-FCC process may be operable to contact the hydrocarbon feed, such as a naphtha or gas condensate feed, with a cracking catalyst under high-severity conditions to produce olefins, such as ethylene, propene, mixed butenes, and other C4+ compounds. A cracking C4 effluent from the HS-FCC process may be further processed in the metathesis process to convert at least a portion of the mixed butenes to ethylene and propene through metathesis of the mixed butenes. Metathesis of a portion of the mixed butenes in the metathesis process to produce ethylene and propene may increase the selectivity and yield of ethylene, propene, or both, from the olefin process. C5+ compounds produced in the metathesis process may be passed back to the HS-FCC process for further conversion, which may further increase the selectivity and yield of ethylene, propene, or both, from the olefin process. The selectivity and yield of ethylene, propene, or both, may be further improved by removing and recovering isobutene from the cracking C4 effluent upstream of the metathesis process.

According to one or more aspects of the present disclosure, a process for producing olefins may include contacting a hydrocarbon feed with a cracking catalyst under high-severity conditions to produce a cracking reaction effluent comprising at least butenes. The high-severity conditions may include a temperature of greater than or equal to 500° C., a residence time of less than 3 seconds, and a cracking catalyst to hydrocarbon weight ratio of greater than 5:1. The process may further include contacting at least a portion of the cracking reaction effluent with a metathesis catalyst, where the contacting may cause metathesis of at least a portion of the butenes in the portion of the cracking reaction effluent to produce a metathesis reaction product. The process may further include separating the metathesis reaction product into a metathesis C5+ effluent and at least one olefin-containing effluent. The olefin-containing effluent may include at least one of ethylene, propene, butenes, or combinations of these. The process may further include contacting the metathesis C5+ effluent with the cracking catalyst and the hydrocarbon feed under high-severity conditions to produce the cracking reaction effluent.

According to one or more other aspects of the present disclosure, a process for producing olefins that includes introducing a hydrocarbon feed to a high-severity fluidized catalytic cracking system and contacting the hydrocarbon feed with a cracking catalyst under high-severity conditions in the high-severity fluidized catalytic cracking system to produce a cracking reaction effluent comprising butene. The high-severity conditions may include a temperature of greater than or equal to 500° C., a residence time of less than or equal to 3 seconds, and a weight ratio of the cracking catalyst to hydrocarbon of 5:1. The process may further include passing at least a portion of the cracking reaction effluent to a metathesis system. The at least a portion of the cracking reaction effluent may include a cracking C4 effluent that includes at least butene. The process may further include contacting the cracking C4 effluent with a metathesis catalyst in the metathesis system, where the contacting may cause at least a portion of the butene in the cracking C4 effluent to undergo a metathesis reaction to produce a metathesis reaction effluent comprising at least one of ethylene, propene, or both. The process may further include separating a metathesis C5+ effluent from the metathesis reaction effluent and passing the metathesis C5+ effluent back to the high-severity fluidized catalytic cracking unit.

According to still other aspects of the present disclosure, a system for producing olefins may include a high-severity fluidized catalytic cracking system comprising a cracking catalyst and operable to contact a hydrocarbon feed with the cracking catalyst under high-severity conditions comprising a temperature of greater than or equal to 500° C., a residence time of less than or equal to 3 seconds, and a weight ratio of cracking catalyst to hydrocarbon of greater than or equal to 5:1 to produce a cracking reaction effluent comprising ethylene, propene, butene, or combinations of these. The system for producing olefins may further include an isobutene removal unit downstream of the high-severity fluidized catalytic cracking system. The isobutene removal unit may be operable to receive a cracking C4 effluent from the high-severity fluidized catalytic cracking system and remove at least a portion of the isobutene from the cracking C4 effluent to produce a metathesis feed having a decreased concentration of isobutene compared to the cracking C4 effluent. The system may further include a metathesis system downstream of the isobutene removal unit. The metathesis system may be operable to contact the metathesis feed with at least a metathesis catalyst to produce a metathesis reaction effluent comprising at least propene, ethylene, or both. The system may further include a C5+ recycle extending from a C5+ outlet of the metathesis system to an inlet of the high-severity fluidized catalytic cracking system, the C5+ recycle operable to pass a metathesis C5+ effluent from the metathesis system back to the high-severity fluidized catalytic cracking system.

Additional features and advantages of the present disclosure will be set forth in the detailed description that follows, and in part will be readily apparent to those skilled in the art from that description or recognized by practicing the described subject matter, including the detailed description that follows, the claims, as well as the appended drawings.

BRIEF DESCRIPTION OF THE DRAWINGS

The following detailed description of specific aspects of the present disclosure can be best understood when read in conjunction with the following drawings, in which like structure is indicated with like reference numerals and in which.

Figure 1:
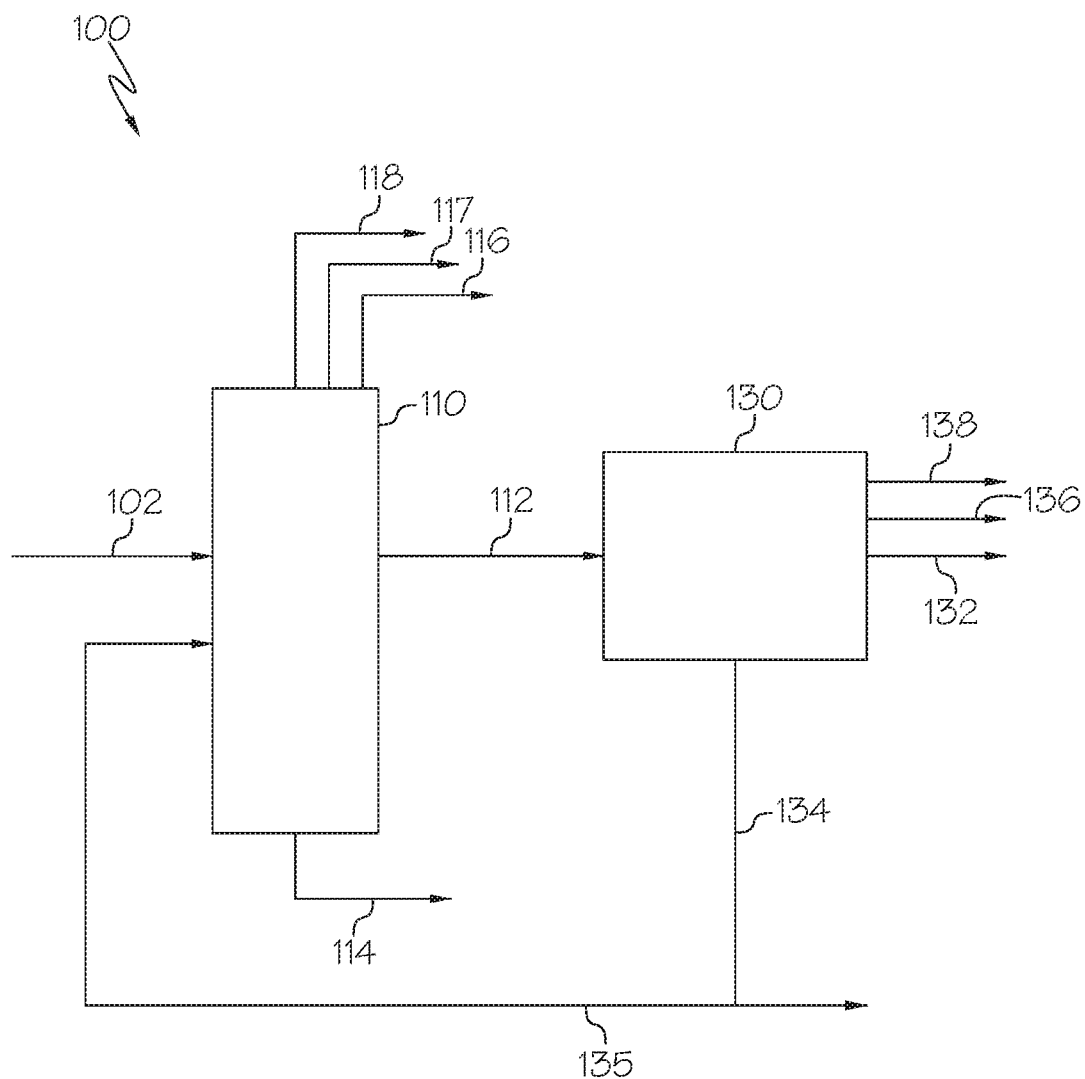
FIG. 1 schematically depicts a process flow diagram for a system for producing olefins, according to one or more embodiments shown and described in the present disclosure.

For purposes of describing the simplified schematic illustrations and descriptions in FIGS. 1-7, the numerous valves, temperature sensors, flow meters, pressure regulators, electronic controllers, pumps, heat exchangers, and the like that may be employed and well known to those of ordinary skill in the art of certain chemical processing operations may not be depicted. Further, accompanying components that are often included in typical chemical processing operations, such as valves, pipes, pumps, agitators, heat exchangers, condensers, boilers, instrumentation, internal vessel structures, or other subsystems may not be depicted. Though not depicted, it should be understood that these components are within the spirit and scope of the present embodiments disclosed. However, operational components, such as those described in the present disclosure, may be added to the embodiments described in this disclosure.

Arrows in the drawings refer to process streams. However, the arrows may equivalently refer to transfer lines, such as pipes or conduits, which may serve to transfer process streams between two or more system components. Additionally, arrows that connect to system components may define inlets or outlets in each given system component. The arrow direction corresponds generally with the major direction of movement of the materials of the stream contained within the physical transfer line signified by the arrow. Furthermore, arrows which do not connect two or more system components may signify a product stream which exits the depicted system component or a system inlet stream which enters the depicted system or system component.

Additionally, arrows in the drawings may schematically depict process steps of transporting a stream or composition from one system component to another system component. For example, an arrow from one system component pointing to another system component may represent "passing" a stream or composition to another system component, which may include the contents of a process stream "exiting" or being "removed" from one system component and "introducing" the contents of that product stream to another system component.

Reference will now be made in greater detail to various aspects of the present disclosure, some aspects of which are illustrated in the accompanying drawings.

DETAILED DESCRIPTION

Figure 4:
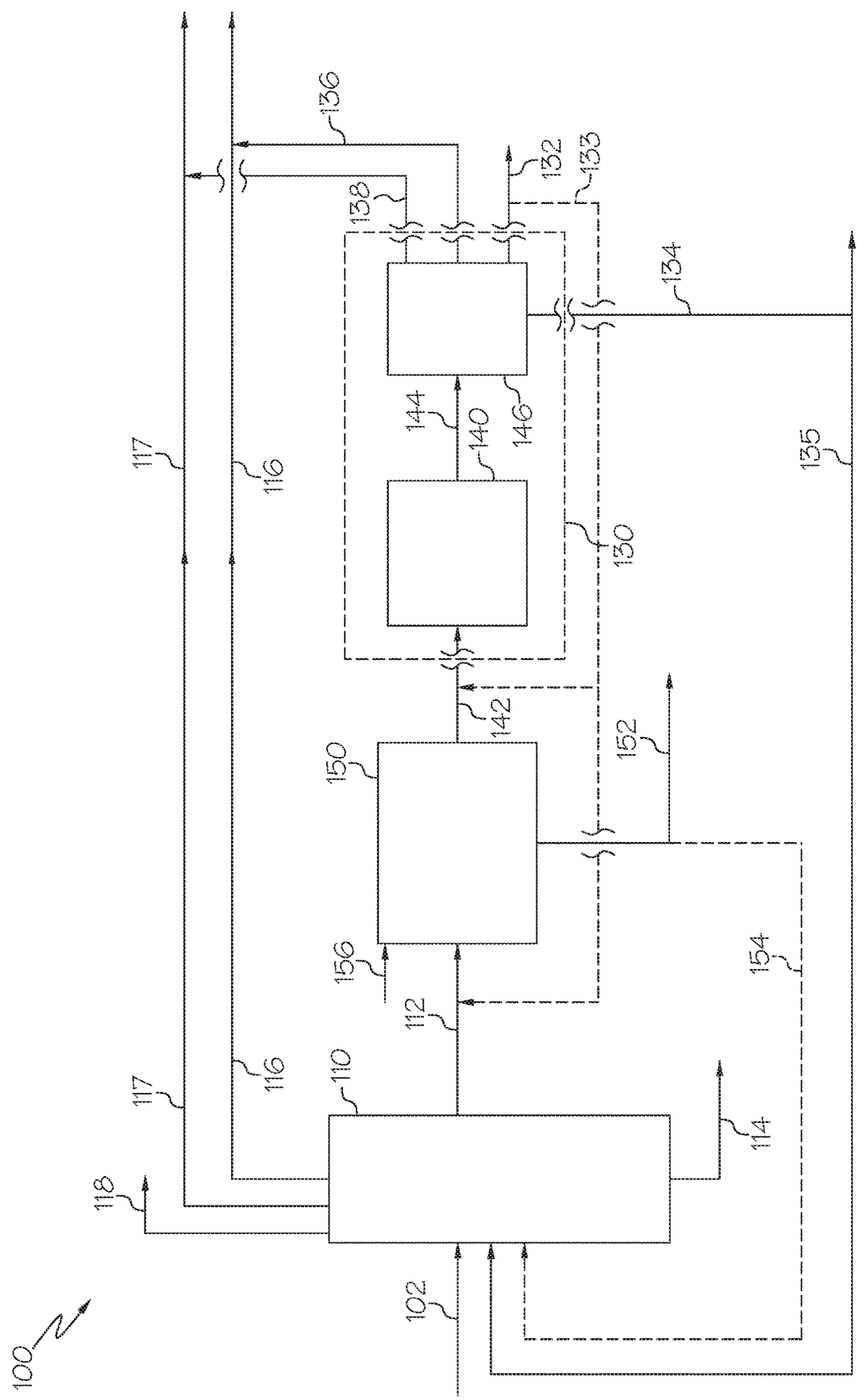
FIG. 4 schematically depicts a process flow diagram of the system of FIG. 1 including an isobutene removal unit disposed between the HS-FCC system and the metathesis system, according to one or more embodiments shown and described in the present disclosure.

The present disclosure is directed to systems and processes for producing olefins from a hydrocarbon feed, such as a naphtha feed or a gas condensate feed. Referring to FIG. 1, one embodiment of a system 100 for producing olefins is depicted. Referring to FIG. 1, the system 100 includes the high-severity fluidized catalytic cracking (HS-FCC) system 110 and the metathesis system 130 disposed downstream of the HS-FCC system 110. The system 100 may also include a metathesis C5+ recycle 135 extending from the metathesis system 130 back to the HS-FCC system 110. The HS-FCC system 110 may include a cracking catalyst and may be operable to contact the hydrocarbon feed 102 with the cracking catalyst under high-severity conditions. The high-severity conditions may include a temperature of greater than or equal to 500° C., a residence time of less than or equal to 3 seconds, and a weight ratio of cracking catalyst to hydrocarbon of greater than or equal to 5:1. Contact of the cracking catalyst with the hydrocarbon feed 102 may convert at least a portion of the hydrocarbon feed 102 to butene to produce a cracking reaction effluent. The metathesis system 130 may be operable to contact at least a portion of the cracking reaction effluent, such as a cracking C4 effluent 112 that includes butene, with a metathesis catalyst to produce a metathesis reaction effluent comprising one or more olefins. The metathesis reaction effluent may be separated into at least a metathesis C5+ effluent 134 and at least one olefin-containing effluent, which may include at least one of ethylene, propene, butene, or combinations of these. The metathesis C5+ recycle 135 may be a conduit fluidly coupled to the metathesis system 130 and the HS-FCC system 110 and may be operable to pass the metathesis C5+ effluent 134 from the metathesis system 130 back to the HS-FCC system 110 for further conversion of hydrocarbons in the metathesis C5+ effluent 134 to light olefins. Referring to FIG. 4, the system 100 may also include an isobutene removal unit 150 downstream of the HS-FCC system 110 and between the HS-FCC system 110 and the metathesis system 130. The isobutene removal unit 150 may be operable to receive the cracking C4 effluent 112 from the HS-FCC system 110 and remove at least a portion of the isobutene in the cracking C4 effluent 112 to produce a metathesis feed 142 having a decreased concentration of isobutene compared to the cracking C4 effluent 112.

Referring again to FIG. 1, a process for producing olefins according to the present disclosure may include contacting the hydrocarbon feed 102 with a cracking catalyst under high-severity conditions to produce a cracking reaction effluent that includes at least butene, where the high-severity conditions include a temperature of greater than or equal to 500° C., a residence time of less than 3 seconds, and a cracking catalyst to hydrocarbon weight ratio of greater than 5:1. The process may further include contacting at least a portion of the butene in the cracking reaction effluent with a metathesis catalyst, where the contacting may cause metathesis of at least a portion of the butene to produce a metathesis reaction product. The process may further include separating the metathesis reaction product into at least a metathesis C5+ effluent 134 and at least one olefin-containing effluent, which may include at least one of ethylene, propene, butene, or combinations of these. The metathesis C5+ effluent 134 may be recycled back into contact with the cracking catalyst and the hydrocarbon feed 102 under the high-severity conditions to produce the cracking reaction effluent. The systems and method of the present disclosure may enable naphtha and gas condensate streams to be used as hydrocarbon feeds to the HS-FCC system 110, and may increase the yield of propene and ethylene from high-severity fluidized catalytic cracking of naphtha and gas condensate feeds.

The term "or", as used in the present disclosure, is inclusive; more specifically, the phrase "A or B" means "A, B, or both A and B." Exclusive "or" is designated in the present disclosure by terms such as "either A or B" and "one of A or B," for example.

The indefinite articles "a" and "an" are employed to describe elements and components of the present disclosure. The use of these articles means that one or at least one of these elements or components is present. Although these articles are conventionally employed to signify that the modified noun is a singular noun, as used herein the articles "a" and "an" also include the plural, unless otherwise stated in specific instances. Similarly, the definite article "the", as used in the present disclosure, also signifies that the modified noun may be singular or plural, again unless otherwise stated in specific instances.

As used throughout the present disclosure, the terms "upstream" and "downstream" refer to the positioning of components or units of the system 100 relative to a direction of flow of materials through the system 100. For example, a first component may be considered "upstream" of a second component if materials flowing through the system 100 encounter the first component before encountering the second component. Likewise, the second component is considered "downstream" of the first component if the materials flowing through the system 100 encounter the first component before encountering the second component.

As used in the present disclosure, reciting that a stream is passed "directly" from an upstream component to a downstream component may refer to passing the stream from the upstream component to the downstream component without passing the stream through an intervening unit operation operable to change the composition or characteristics of the stream. Intervening unit operations can include reactors and separation units but are not generally intended to include heat exchangers, valves, pumps, sensors, or other ancillary process equipment required for operation of a chemical process.

As used in the present disclosure, the term "fluid" may be used to refer to a flowable composition that includes gases, liquids, or a combination of these.

As used throughout the present disclosure, a "reactor" refers to a vessel in which one or more chemical reactions may occur between one or more reactants optionally in the presence of one or more catalysts. For example, a reactor may include a tank or tubular reactor configured to operate as a batch reactor, a continuous stirred-tank reactor (CSTR), a plug flow reactor, a packed bed reactor, a fluidized bed reactor, continuous fluidized bed reactor, a riser reactor, downer reactor, or other type of reactor. One or more "reaction zones" may be disposed in a reactor. As used in this disclosure, a "reaction zone" may refer to a region where a particular reaction takes place in a reactor. For example, a packed bed reactor with multiple catalyst beds may have multiple reaction zones, where each reaction zone is defined by the region occupied by one of the catalyst beds. In another non-limiting example, a multi-stage catalyst reaction system may include multiple reactors, and each reactor may define a separate "reaction zone."

As used throughout the present disclosure, the terms "separation unit" and "separator" may be interchangeable and refer to any separation device that at least partially separates one or more chemicals that are mixed in a process stream from one another. For example, a separation unit may selectively separate differing chemical species from one another, forming one or more chemical fractions. Examples of separation units include, without limitation, distillation columns, flash drums, knock-out drums, knock-out pots, centrifuges, cyclones, filtration devices, traps, scrubbers, expansion devices, adsorption units, membrane separation units, solvent extraction devices, and the like. As used throughout the present disclosure, the term "separation system" may refer to a system that may include one or a plurality of separation units.

It should be understood that separation units and separation systems described in this disclosure may not completely separate all of one chemical constituent from all of another chemical constituent. It should be understood that the separation units and separation systems described in this disclosure "at least partially" separate different chemical components from one another, and that even if not explicitly stated, it should be understood that separation may include only partial separation. As used in this disclosure, one or more chemical constituents may be "separated" from a process stream to form a new process stream. Generally, a process stream may enter a separation unit and be divided, or separated, into two or more process streams of different compositions. A process stream passed out of a separation unit or separation system may be designated using the name of a certain compound or class of compounds and may be considered to include a greater proportion of that certain compound or class of compounds relative to other streams passed out of the separation unit or separation system. It is understood, however, that the other streams passed out of the separation unit or separation system may also include some amounts of the certain compound or class of compounds.

As used throughout the present disclosure, the term "high-severity conditions" may refer to operating conditions in the HS-FCC system 110 that include temperatures of greater than or equal to 500 degrees Celsius (° C.) or greater, a weight ratio of cracking catalyst to hydrocarbon feed (catalyst to oil ratio) of equal to or greater than 5:1, and a residence time of less than or equal to 3 seconds (sec), all of which may be more severe than typical FCC reaction conditions. As used throughout the present disclosure, the term "residence time" may refer to the amount of time that the reactants are in contact with the catalyst at reaction conditions, such as at the reaction temperature, in a reaction system. As a non-limiting example, the residence time in the HS-FCC reactor 220 may refer to the time that the hydrocarbons of the hydrocarbon feed 102 are in contact with the cracking catalyst at the reaction temperature of greater than or equal to 500° C., such as from 500° C. to 800° C.

As used throughout the present disclosure, the term "effluent" may refer to a stream that exits a system component such as a separation unit, a reactor, or reaction zone, following a particular reaction or separation, and generally has a different composition (at least proportionally) than the stream that entered the separation unit, reactor, or reaction zone.

As used throughout the present disclosure, a "catalyst" may refer to any substance that increases the rate of a specific chemical reaction. Catalysts described in this disclosure may be utilized to promote various reactions, such as, but not limited to, cracking reactions, metathesis reactions, isomerization reactions, hydration reactions, etherification reactions, or other chemical reaction.

As used in this disclosure, "cracking" may generally refer to a chemical reaction where a molecule having carbon to carbon bonds is broken into more than one molecule by the breaking of one or more of the carbon to carbon bonds, or is converted from a compound which includes a cyclic moiety, such as a cycloalkane, cycloalkene, naphthalene, an aromatic or the like, to a compound which does not include a cyclic moiety or contains fewer cyclic moieties than prior to cracking.

It should further be understood that streams may be named for the components of the stream, and the component for which the stream is named may be the major component of the stream (such as comprising from 50 weight percent (wt. %), from 70 wt. %, from 90 wt. %, from 95 wt. %, from 99 wt. %, from 99.5 wt. %, or even from 99.9 wt. % of the contents of the stream to 100 wt. % of the contents of the stream). It should also be understood that components of a stream are disclosed as passing from one system component to another when a stream comprising that component is disclosed as passing from that system component to another. For example, a disclosed "cracking C4 effluent" passing from a first system component to a second system component should be understood to equivalently disclose the "cracking C4 effluent" passing from a first system component to a second system component.

As used in the present disclosure, the terms "butenes" or "mixed butenes" may be used interchangeably and may refer to combinations of one or a plurality of isobutene, 1-butene, trans-2-butene, or cis-2-butene. As used in the present disclosure, the term "normal butenes" may refer to a combination of one or a plurality of 1-butene, trans-2-butene, or cis-2-butene.

Referring again to FIG. 1, the system 100 for producing olefins, such as but not limited to propene and ethylene, may include the HS-FCC system 110, the metathesis system 130 downstream of the HS-FCC system 110, and the metathesis C5+ recycle 135 fluidly coupled to the metathesis system 130 and the HS-FCC system 110. The HS-FCC system 110 may be operable to contact the hydrocarbon feed 102 with a cracking catalyst under high-severity conditions to produce a cracking reaction effluent.

The hydrocarbon feed 102 may generally include a mixture of hydrocarbon materials. The hydrocarbon materials of the hydrocarbon feed 102 may include hydrocarbons derived from crude oil. As used in this disclosure, the term "crude oil" may be understood to mean a mixture of petroleum liquids and gases, including impurities such as sulfur-containing compounds, nitrogen-containing compounds and metal compounds, as distinguished from fractions of crude oil. The hydrocarbon feed 102 may include, but may not be limited to, crude oil, vacuum residue, tar sands, bitumen, atmospheric residue, vacuum gas oils, demetalized oils, naphtha streams, gas condensate streams, or combinations of these materials. The hydrocarbon feed stream 102 may include one or a plurality of non-hydrocarbon constituents, such as one or more heavy metals, sulphur compounds, nitrogen compounds, inorganic components, or other non-hydrocarbon compounds. In one or more embodiments, the hydrocarbon feed 102 may be a naphtha stream, a gas condensate stream, or a combination of these. As used in the present disclosure, the term "naphtha" may refer to an intermediate hydrocarbon composition derived from crude oil refining and having a boiling point temperature of from 35° C. to 200° C. Naphtha streams may include paraffinic, naphthenic, and aromatic hydrocarbons having from 4 to 11 carbon atoms. As used in the present disclosure, the term "gas condensate" may refer to a mixture of liquid hydrocarbons having a specific gravity of from 0.5 to 0.8 and derived from raw natural gas produced from natural gas fields. Gas condensates may include paraffinic hydrocarbons having from 3 to 12 carbon atoms and lesser amounts of naphthenic and aromatic compounds compared to naphtha streams. Hydrocarbons with greater than 12 carbon atoms may also be present. The gas condensate may include at least 70 wt. %, at least 75 wt. %, or even at least 80 wt. % hydrocarbons having a boiling point temperatures less than 265° C. The gas condensates may have greater boiling hydrocarbons recovered from raw natural gas as a condensate in a natural gas processing plant. In embodiments, the gas condensate may be a Khuff gas condensate recovered from natural gas extracted from the Khuff reservoir in Saudi Arabia. Table 1 provides boiling point profile data for Khuff gas condensate.

TABLE 1

Boiling Point Temperature Profile for Khuff Gas Condensate

| Boiling Point (BP) Temperature Range | | Weight | Cummulative | Volume |
|---|---|---|---|---|
| Initial BP (° C.) | Final BP (° C.) | Percent wt. % | Weight Percent wt. % | Percent vol. % |
| C5 (35) | 70 | 12.9 | 12.9 | 15.36 |
| 70 | 185 | 47.32 | 60.22 | 48.15 |
| 185 | 265 | 19.9 | 80.12 | 18.79 |
| 265 | 345 | 12.14 | 92.26 | 10.99 |
| 345 | 460 | 6.87 | 99.13 | 6.04 |
| 460 | 565 | 0.29 | 99.42 | 0.25 |
| 565 | 1000 | 0.56 | 99.98 | 0.41 |

In one or more embodiments, one or more supplemental feed streams (not shown) may be added to the hydrocarbon feed 102 prior to introducing the hydrocarbon feed 102 to the HS-FCC system 110 or introduced independently to the HS-FCC system 110 in addition to the hydrocarbon feed 102. For example, the hydrocarbon feed 102 may include a naphtha stream, a gas condensate, or a combination of these, and a supplemental stream, such as one or a plurality of a vacuum residue, atmospheric residue, vacuum gas oils, demetalized oils, or other hydrocarbon streams, or combinations of these materials, may be combined with the hydrocarbon feed 102 upstream of the HS-FCC system 110 or introduced independently to the HS-FCC system 110.

Figure 2:
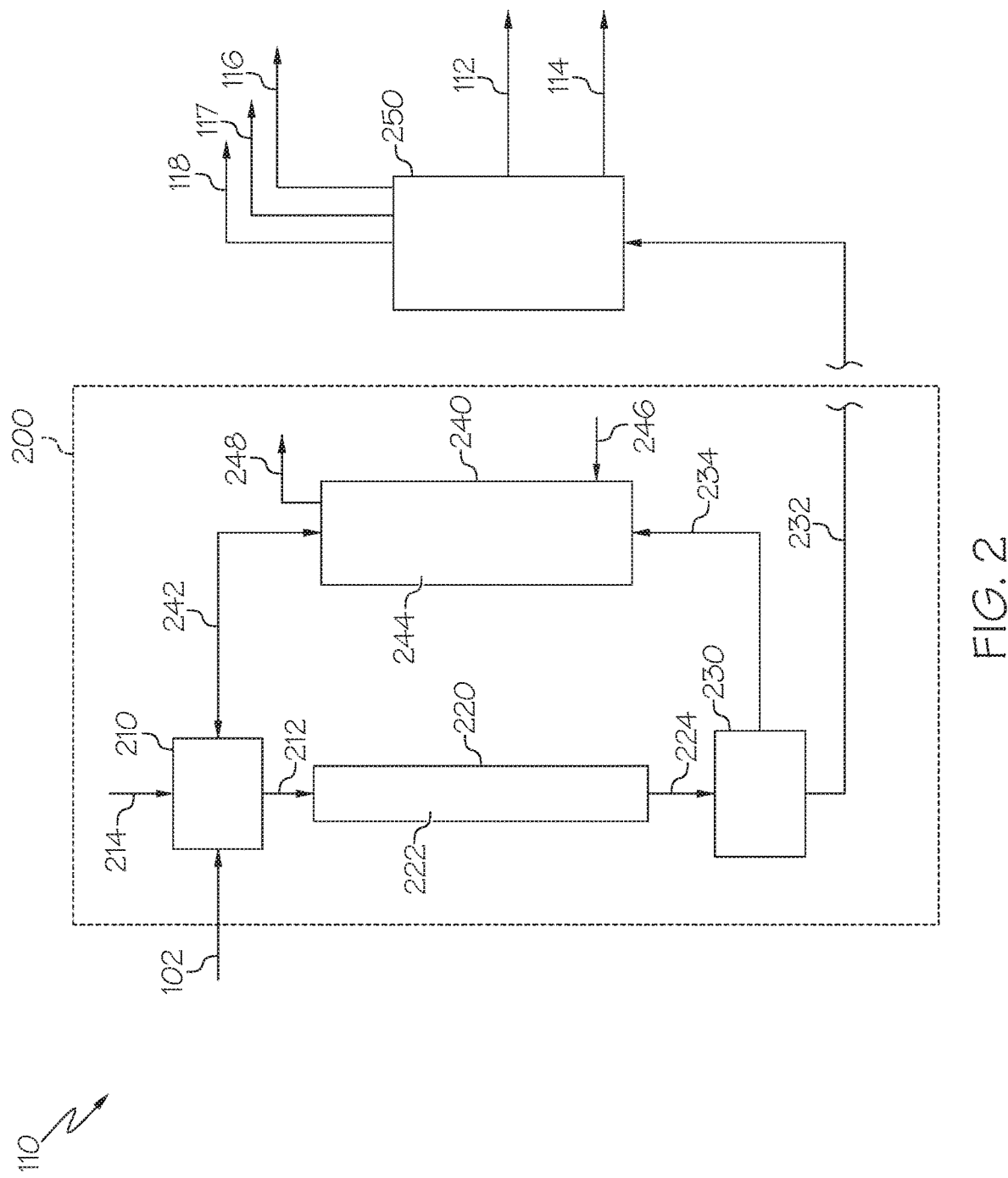
FIG. 2 schematically depicts a process flow diagram for a high-severity fluidized catalytic cracking (HS-FCC) system of the system for producing olefins of FIG. 1, according to one or more embodiments shown and described in the present disclosure.

Referring now to FIG. 2, the HS-FCC system 110 may include an HS-FCC reactor unit 200 and a cracking effluent separation system 250 downstream of the HS-FCC reactor unit 200. The HS-FCC reactor unit 200 may include a mixing zone 210, an HS-FCC reactor 220 downstream of the mixing zone 210, a cracking catalyst separator 230 downstream of the HS-FCC reactor 220, and a cracking catalyst regenerator 240. The mixing zone 210 may be operable to receive the hydrocarbon feed 102, and any supplemental feed streams, and combine the hydrocarbon feed 102 with a cracking catalyst to form a mixed catalyst hydrocarbon stream 212. The cracking catalyst may include regenerated cracking catalyst 242, new cracking catalyst 214, or combinations of regenerated catalyst 242 and new cracking catalyst 214. For example, new cracking catalyst 214 may be added to the mixing zone 210 during initial startup of the HS-FCC reactor unit 200. New cracking catalyst 214 may be added to the mixing zone 210 during steady-state operation to replenish cracking catalyst lost due to attrition or removed due to permanent deactivation.

The cracking catalyst may include one or a plurality of fluid catalytic cracking catalysts that are suitable for use under the high-severity conditions in the HS-FCC reactor 220. The cracking catalyst may be a heat carrier and may provide heat transfer to the hydrocarbon feed 102 in the HS-FCC reactor 220 operated at high-severity conditions. The cracking catalyst may also have a plurality of catalytically active sites, such as acidic sites for example, that promote the cracking reactions. As a non-limiting example, in one or more embodiments, the catalyst may be a high-activity FCC catalyst having greater catalytic activity compared to cracking catalysts that serve mainly as heat carriers to maintain the reaction temperature. Examples of fluid catalytic cracking catalysts suitable for use in the HS-FCC reactor unit 200 may include, without limitation, zeolites, silica-alumina catalysts, carbon monoxide burning promoter additives, bottoms cracking additives, light olefin-producing additives, other catalyst additives, or combinations of these components. Zeolites that may be used as at least a portion of the cracking catalyst may include, but are not limited to, Y, REY, USY, RE-USY zeolites, or combinations of these. The cracking catalyst may also include a shaped-selective catalyst additive, such as ZSM-5 zeolite crystals or other pentasil-type catalyst structures, which are often used in other FCC processes to produce light olefins, increase FCC gasoline octane, or both. In one or more embodiments, the catalyst may include a mixture of a ZSM-5 zeolite crystals and the cracking catalyst zeolite and matrix structure of a typical FCC cracking catalyst. In one or more embodiments, the catalyst may be a mixture of Y and ZSM-5 zeolite catalysts embedded with clay, alumina, and binder.

In one or more embodiments, at least a portion of the cracking catalyst may be modified to include one or more rare earth elements (15 elements of the Lanthanide series of the International Union of Pure and Applied Chemistry (IUPAC) Periodic Table plus scandium and yttrium), alkaline earth metals (Group 2 of the IUPAC Periodic Table), transition metals, phosphorus, fluorine, or any combination of these, which may enhance olefin yield in the HS-FCC reactor unit 200. Transition metals may include "an element whose atom has a partially filled d sub-shell, or which can give rise to cations with an incomplete d sub-shell" [IUPAC, Compendium of Chemical Terminology, 2nd ed. (the "Gold Book") (1997). Online corrected version: (2006-) "transition element"]. One or more transition metals or metal oxides may also be impregnated onto the catalyst. Metals or metal oxides may include one or more metals from Groups 6-10 of the IUPAC Periodic Table. In some embodiments, the metals or metal oxides may include one or more of molybdenum, rhenium, tungsten, or any combination of these. In one or more embodiments, a portion of the catalyst may be impregnated with tungsten oxide.

Referring again to FIG. 2, the hydrocarbon feed 102 and the cracking catalyst may be mixed in the mixing zone 210 to produce a mixed catalyst hydrocarbon stream 212. The mixed catalyst hydrocarbon stream 212 may have a weight ratio of the cracking catalyst to hydrocarbons from the hydrocarbon feed 102 (catalyst to hydrocarbon weight ratio) sufficient for high-severity fluidized catalytic cracking, such as greater than or equal to 5:1, greater than or equal to 10:1, greater than or equal to 15:1, or even greater than or equal to 25:1. When the weight ratio of the cracking catalyst to hydrocarbons is less than 5:1, the conversion of hydrocarbons through catalytic cracking may be reduced due to lesser reactive catalyst sites available in the reactor. This can lead to a shift to a greater degree of thermal cracking relative to catalytic cracking, which can change the composition of the cracking reaction effluent. The mixed catalyst hydrocarbon stream 212 may have a weight ratio of cracking catalyst to hydrocarbons from the hydrocarbon feed 102 of less than or equal to 40:1, less than or equal to 35:1, less than or equal to 30:1, less than or equal to 25:1, less than or equal to 15:1, or less than or equal to 10:1. The mixed catalyst hydrocarbon stream 212 may have a weight ratio of the cracking catalyst to hydrocarbons in the hydrocarbon feed 102 of from 5:1 to 40:1, from 5:1 to 35:1, from 5:1 to 30:1, from 5:1 to 25:1, from 5:1 to 15:1, from 5:1 to 10:1, from 10:1 to 40:1, from 10:1 to 35:1, from 10:1 to 30:1, from 10:1 to 25:1, from 10:1 to 15:1, from 15:1 to 40:1, from 15:1 to 35:1, from 15:1 to 30:1, from 15:1 to 25:1, from 25:1 to 40:1, from 25:1 to 35:1, from 25:1 to 30:1, or from 30:1 to 40:1.

The mixed catalyst hydrocarbon stream 212 may be passed from the mixing zone 210 to the HS-FCC reactor 220. The HS-FCC reactor 220 may be a downflow reactor or "downer" reactor in which the mixed catalyst hydrocarbon stream 212 flows from the mixing zone 210 vertically downward through the cracking reaction zone 222 of the HS-FCC reactor 220. Steam (not shown) may be introduced to the top portion of the HS-FCC reactor 220 to provide additional heating to the mixed catalyst hydrocarbon stream 212. Although shown in FIG. 2 as being a "downer" reactor, the HS-FCC reactor 220 may also be a riser reactor in which the mixed catalyst hydrocarbon stream 212 flows upward through the HS-FCC reactor 220. The HS-FCC reactor 220 may define a cracking reaction zone 222 in which the hydrocarbons from the hydrocarbon feed 102 are contacted with the cracking catalyst under high-severity conditions. Contact between the hydrocarbons from the hydrocarbon feed 102 and the cracking catalyst in the HS-FCC reactor 220 under high-severity conditions may cause the at least a portion of the hydrocarbons from the hydrocarbon feed 102 to react, such as undergoing at least a cracking reaction, to produce an HS-FCC reactor outlet stream 224, which may be a mixture of a cracking reaction product and used cracking catalyst. Used cracking catalyst may refer to cracking catalyst having decreased catalytic activity (ability to promote the cracking reactions) compared to new or regenerated cracking catalyst. The reduced catalytic activity of the used cracking catalyst may be due to coke deposits, reduced temperature, or a combination of both.

The HS-FCC reactor 220 may be operated at high-severity conditions. The HS-FCC reactor 220 may be operated at a temperature of greater than or equal to 500° C., such as greater than or equal to 550° C., or even greater than or equal to 600° C. The HS-FCC reactor 220 may be operated at a temperature of less than or equal to 800° C., such as less than or equal to 700° C., or even less than or equal to 650° C. The HS-FCC reactor 220 may be operated at a temperature of the cracking reaction zone 222 of from 500° C. to 800° C., from 500° C. to 700° C., from 500° C. to 650° C., from 500° C. to 600° C., from 550° C. to 800° C., from 550° C. to 700° C., from 550° C. to 650° C., from 550° C. to 600° C., from 600° C. to 800° C., from 600° C. to 700° C., or from 600° C. to 650° C. In one or more embodiments, the temperature of the cracking reaction zone 222 in the HS-FCC reactor 220 may be from 500° C. to 700° C. In one or more embodiments, temperature of the cracking reaction zone 222 in the HS-FCC reactor 220 may be from 550° C. to 630° C. The temperature of the cracking reaction zone 222 in the HS-FCC reactor 220 may be maintained by heating the cracking catalyst to a catalyst temperature greater than the temperature in the cracking reaction zone 222 prior to mixing the cracking catalyst with the hydrocarbon feed 102 to produce the mixed catalyst hydrocarbon stream 212. Additionally, in one or more embodiments, steam may also be introduced to the HS-FCC reactor 220 to maintain the temperature in the cracking reaction zone 222 in high-severity conditions.

The flowrate of the mixed catalyst hydrocarbon stream 212 through the cracking reaction zone 222 of the HS-FCC reactor 220 may be sufficient to produce a residence time of the hydrocarbons from the hydrocarbon feed 102 in contact with the cracking catalyst at reaction temperatures of less than or equal to 3 seconds (sec), such as less than or equal to 2.5 sec, less than or equal to 2.0 sec, or even less than or equal to 1.5 sec. When the residence time is greater than 3 seconds at the reaction temperature, excessive thermal cracking may occur, which may overly crack the hydrocarbons from the hydrocarbon feed 102 and reduce the selectivity towards olefins, such as propene, ethylene, and butene. The residence time of the mixed catalyst hydrocarbon stream 212 in the cracking reaction zone 222 of the HS-FCC reactor 220 may be greater than or equal to 0.2 sec, greater than or equal to 0.4 sec, or even greater than or equal to 1.0 sec. When the residence time is less than about 0.2 seconds, insufficient catalytic cracking may occur, which may result is decreased selectivity to olefins. The residence time of the mixed catalyst hydrocarbon stream 212 in the cracking reaction zone 222 of the HS-FCC reactor 220 may be from 0.2 sec to 3 sec, from 0.2 sec to 2.5 sec, from 0.2 sec to 2 sec, from 0.2 sec to 1.5 sec, from 0.4 sec to 3 sec, from 0.4 sec to 2.5 sec, or from 0.4 sec to 2 sec, from 0.4 sec to 1.5 sec, from 1.0 sec to 3 sec, from 1.0 sec to 2.5 sec, from 1.0 sec to 2 sec, or from 2 sec to 3 sec.

Referring again to FIG. 2, the HS-FCC reactor outlet stream 224 may be passed from the HS-FCC reactor 220 to the cracking catalyst separator 230, which may be disposed downstream of the HS-FCC reactor 220. In the cracking catalyst separator 230, the HS-FCC reactor outlet stream 224 may be separated into a used cracking catalyst stream 234 and a cracking reaction effluent 232. The cracking catalyst separator 230 may include a gas-solid separator operable to mechanically separate the used cracking catalyst from at least a portion of the cracking reaction products. Examples of a gas-solid separator may include but are not limited to cyclones, deflectors, or combinations of these. After separation from the gases of the HS-FCC reactor outlet stream 224, the used cracking catalyst may retain a residual portion of the cracking reaction products. The cracking catalyst separator 230 may also include a stripping zone (not shown), in which a stripping gas, such as steam, is passed through the used cracking catalyst to remove at least some of the residual portion of the cracking reaction products retained by the used cracking catalyst. The stripping gases and cracking reaction products may be combined to form the cracking reaction effluent 232, which may be passed to one or a plurality of downstream unit operations, such as the metathesis system 130, the isobutene removal unit 150, cracking effluent separation system 250, or combinations of these, for further processing.

The used cracking catalyst stream 234 may be passed to the cracking catalyst regenerator 240. The cracking catalyst regenerator 240 may be operable to regenerate the used cracking catalyst stream 234 to produce the regenerated catalyst 242. The cracking catalyst regenerator 240 may include a regeneration zone 244. Combustion gases 246 may be introduced to the regeneration zone 244. The combustion gases 246 may include one or more of combustion air, oxygen, fuel gas, fuel oil, other components, or any combinations of these. In the regeneration zone 244, at least a portion of the coke deposited on the used cracking catalyst in the HS-FCC reactor 220 may oxidize (combust) in the presence of the combustion gases 246 to form at least carbon dioxide and water. In some embodiments, the coke deposits on the used cracking catalyst may be fully oxidized in the regeneration zone 244. Other organic compounds, such as but not limited to any cracking reaction products remaining in the pores of the used cracking catalyst, may also oxidize in the presence of the combustion gases 246 in the regeneration zone 244. Other gases, such as carbon monoxide for example, may be formed during coke oxidation in the regeneration zone 244.

Oxidation of the coke deposits produces heat, which may be transferred to and retained by the regenerated catalyst 242. Thus, regeneration of the used cracking catalyst may include increasing the temperature of the regenerated catalyst 242 above the operating temperature of the HS-FCC reactor 220 in addition to removing coke deposits. In some instances, combustion of the coke deposits on the used cracking catalyst may be sufficient to increase the temperature of the regenerated catalyst 242 to a catalyst temperature greater than the operating temperature of the HS-FCC reactor 220, such as greater than 500° C. However, under some operating conditions and feed compositions, the coke deposits on the used cracking catalyst may not be sufficient to increase the temperature above the operating temperature of the HS-FCC reactor 220. In these cases, a combustion fuel such as but not limited to fuel gas or fuel oil, may be introduced to the regeneration zone 244 of the cracking catalyst regenerator 240 to increase the heat transferred to the regenerated catalyst 242. The regenerated catalyst 242 may be passed from the cracking catalyst regenerator 240 to the mixing zone 210. The cracking catalyst regenerator 240 may include one or a plurality of catalyst hoppers (not shown) in which the regenerated catalyst 242 may accumulate before being combined with the hydrocarbon feed 102 in the mixing zone 210.

The HS-FCC reactor unit 200 is shown in FIG. 2 as comprising a single HS-FCC reactor 220. However, the HS-FCC reactor unit 200 may also include a plurality of HS-FCC reactors 220 operated in parallel or in series. When the HS-FCC reactor unit 200 includes a plurality of HS-FCC reactors 220, the HS-FCC reactor unit 200 may also include a plurality of mixing zones 210, a plurality of cracking catalyst separators 230, a plurality of cracking catalyst regenerators 240, or combinations of these. Various heat transfer devices, separation systems, or other unit operations may be employed in the HS-FCC reactor unit 200 having a plurality of HS-FCC reactors 220.

Referring to FIG. 2, the cracking reaction effluent 232 may be passed to the cracking effluent separation system 250. The cracking reaction effluent 232 may include a mixture of cracked hydrocarbon materials. In particular, the cracking reaction effluent 232 may include one or a plurality of C4 compounds, such as but not limited to mixed butenes (1-butene, trans-2 butene, cis-2-butene, isobutene). The cracking reaction effluent 232 may also include one or a plurality of fuel oil, gasoline, butadiene, propene, ethylene, methane, ethane, propane, butane, pentane, other C5+ hydrocarbons, light cycle oil (LCO, 216-343° C.), heavy cycle oil (HCO, >343° C.), other compounds, or combinations of these. The cracking reaction effluent 232 may also include other gases from the HS-FCC reactor unit 200, such as steam introduced to the HS-FCC reactor 220 or stripping gases from the cracking catalyst separator 230.

The cracking effluent separation system 250 may be fluidly coupled to the HS-FCC reactor unit 200 such that the cracking reaction effluent 232 may be passed directly from the HS-FCC reactor unit 200 to the cracking effluent separation system 250. The cracking effluent separation system 250 may be operable to separate the cracking reaction effluent 232 into a plurality of cracking effluent streams that include at least a cracking C4 effluent 112. The cracking effluent separation system 250 may include one or a plurality of separation units operable to separate the cracking reaction effluent 232 into a plurality of cracking effluents. Separation units may include, but are not limited to, flash drums, high-pressure separators, distillation units, fractional distillation units, condensing units, strippers, quench units, debutanizers, depropanizers, de-ethanizers, or combinations of these. In one or more embodiments, the cracking effluent separation system 250 may include a fractional distillation unit operable to separate the cracking reaction effluent 232 to produce at least the cracking C4 effluent 112. The cracking C4 effluent 112 may include one or a plurality of n-butane, isobutane, butadiene, mixed butenes (1-butene, trans-2-butene, cis-2-butene), isobutene, or combinations of these. The cracking C4 effluent 112 may also include small amounts of one or more other compounds present in the cracking reaction effluent 232. The cracking C4 effluent 112 may include at least 90%, at least 95%, at least 98%, or even at least 99% by weight of the C4 compounds from the cracking reaction effluent 232.

The cracking effluent separation system 250 may also be operable to separate the cracking reaction effluent 232 into a greater boiling temperature effluent 114, a cracking propene effluent 116, a cracking ethylene effluent 117, a lesser molecular weight gas effluent 118, or combinations of these. The greater boiling temperature effluent 114 may include constituents of the cracking reaction effluent 232 having a boiling point temperature greater than the boiling point temperatures of the constituents of the cracking C4 effluent 112. The greater boiling temperature effluent 114 may include one or a plurality of fuel oil, gasoline, pentane, other C5+ hydrocarbons, light cycle oil (LCO, having a boiling point temperature of 216° C. to 343° C.), heavy cycle oil (HCO, having a boiling point temperature of greater than 343° C.), other compounds, or combinations of these. The greater boiling temperature effluent 114 may also include small amounts of C4 hydrocarbons not separated into the cracking C4 effluent 112. The cracking propene effluent 116 may include propene as a primary component. The cracking ethylene effluent 117 may include ethylene as a primary component. The lesser molecular weight gas effluent 118 may include other lesser boiling gases from the cracking reaction effluent 232, such as but not limited to methane, ethane, propane, hydrogen, steam, or other gases having a boiling point temperature less than ethylene and propene. One or a plurality of the greater boiling temperature effluent 114, cracking propene effluent 116, cracking ethylene effluent 117, lesser molecular weight gas effluent 118, or combinations of these may be passed to one or more additional downstream unit operations for further processing. For example, the greater boiling temperature effluent 114 may be passed to another separation unit for separation into one or a plurality of a gasoline stream, a fuel oil stream, a light cycle oil stream, a heavy cycle oil stream, other stream, or combinations of these.

Referring again to FIG. 1, the system 100 includes the metathesis system 130 disposed downstream of the HS-FCC system 110. The metathesis system 130 may be operable to contact a metathesis feed, such as at least a portion of the cracking C4 effluent 112, with at least a metathesis catalyst to produce a metathesis reaction effluent comprising one or more olefins, such as but not limited to ethylene, propene, pentene, or combinations of these. The metathesis system 130 may be operable to contact the metathesis feed with a multiple catalyst system comprising a metathesis catalyst and a cracking catalyst downstream of the metathesis catalyst to produce the metathesis reaction effluent. The metathesis system 130 may also be operable to separate the metathesis reaction effluent into one or more metathesis effluent streams.

Figure 3:
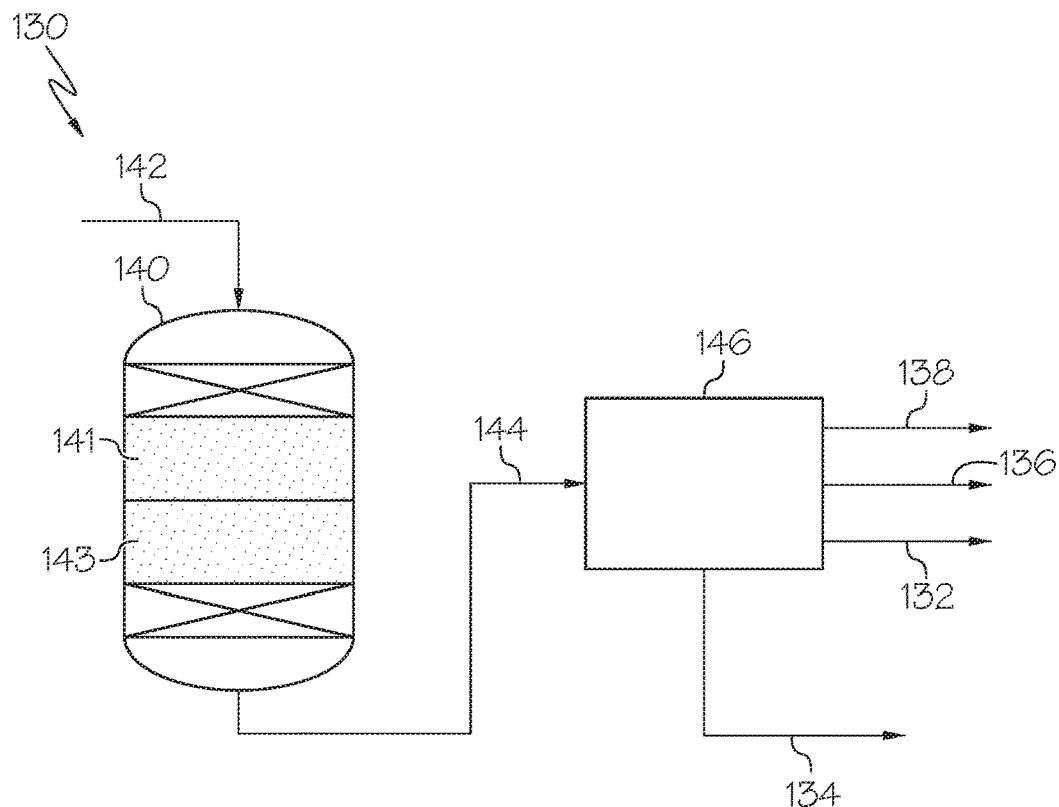
FIG. 3 schematically depicts a process flow diagram for a metathesis system of the system for producing olefins of FIG. 1, according to one or more embodiments shown and described in the present disclosure.
Figure 7:
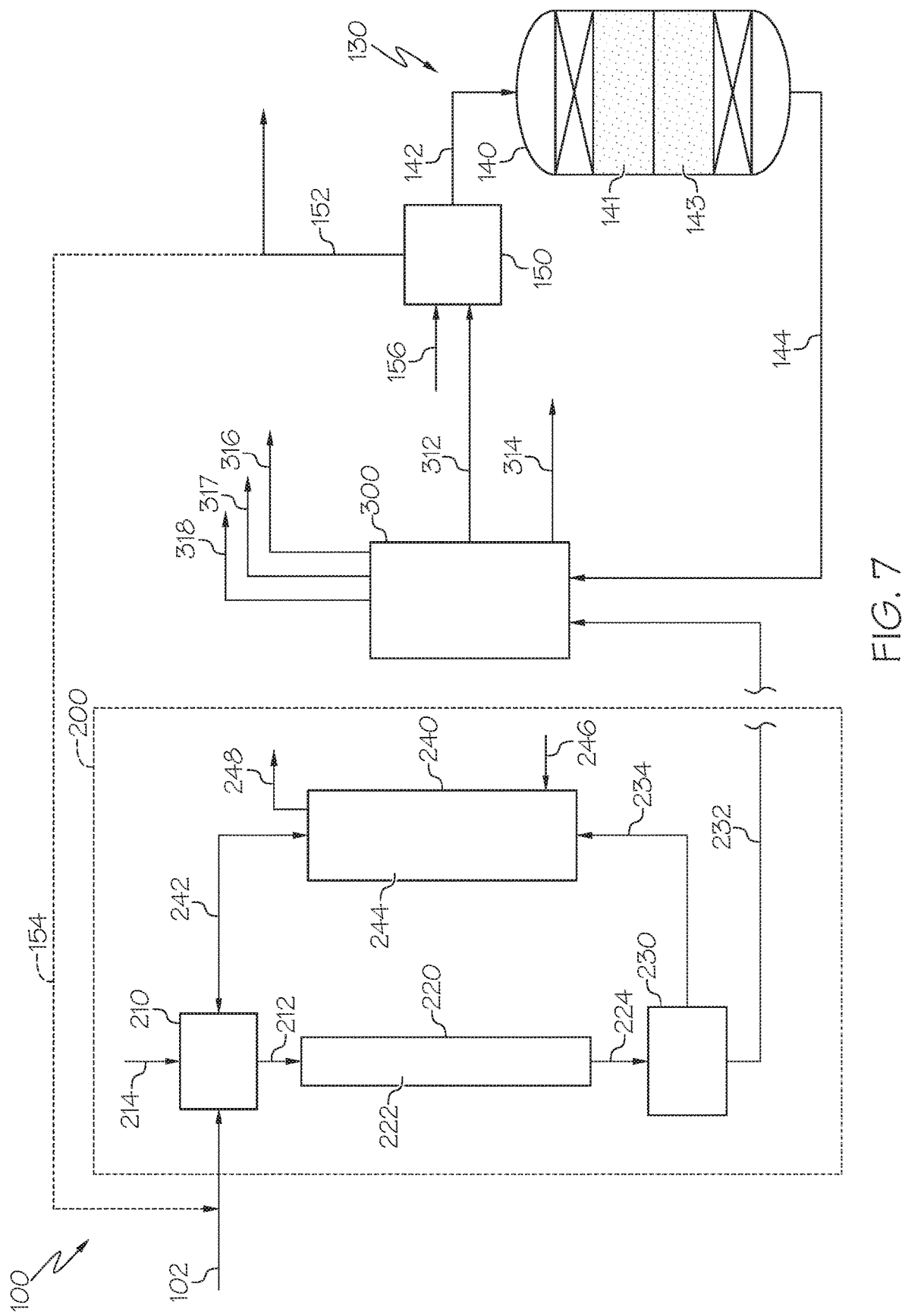
FIG. 7 schematically depicts a process flow diagram of still another system for producing olefins, according to one or more embodiments shown and described in the present disclosure.

Referring now to FIG. 3, the metathesis system 130 may include a metathesis reactor 140 and a metathesis effluent separation system 146 downstream of the metathesis reactor 140. The metathesis reactor 140 may be operable to receive a metathesis feed 142 and contact the metathesis feed 142 with at least the metathesis catalyst, where contacting the metathesis feed 142 with the metathesis catalyst may cause at least a portion of the mixed butenes from the metathesis feed 142 to undergo at least a metathesis reaction to produce a metathesis effluent 144 that includes one or more metathesis reaction products. The metathesis reactor 140 may also be operable to contact the metathesis feed 142 with the metathesis catalyst and a cracking catalyst downstream of the metathesis catalyst. The metathesis effluent separation system 146 may be operable to receive the metathesis effluent 144 from the metathesis reactor 140 and separate the metathesis reaction effluent 144 into one or a plurality of metathesis effluent streams. Alternatively, the metathesis effluent 144 and the cracking reaction effluent 232 may be passed to a single separation system, such as but not limited to the cracking effluent separation system 250 (FIG. 2) or to a combined separation system 300 (FIG. 7).

As used throughout the present disclosure, "metathesis" refers to an organic reaction that involves the redistribution of fragments of alkenes by the scission and regeneration of carbon-carbon double bonds. As used throughout the present disclosure, a "metathesis catalyst" may refer to a catalyst that promotes the metathesis reaction of alkenes to form other alkenes. Contact of butenes with a metathesis catalyst may result in conversion 2-butene to 1-butene or conversion to 1-butene to 2-butene through "self-metathesis," which is shown in Chemical Reaction 1 (RXN 1). Self-metathesis of 2-butene to 1-butene and 1-butene to 2-butene by the metathesis catalyst may be an equilibrium reaction as denoted by bi-directional arrows with single heads in RXN 1.

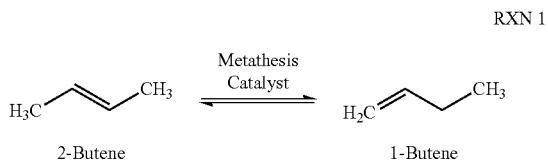

RXN 1

Contact of a mixture of normal butenes (1-butene, trans-2-butene, cis-2-butene, or combinations of these) with the metathesis catalyst may also result in cross-metathesis of 1-butene and 2-butene. As used in the present disclosure, the term "2-butene" may refer to trans-2-butene, cis-2-butene, or a mixture of these. Cross-metathesis between 1-butene and 2-butene may be achieved with the metathesis catalyst as shown in Chemical Reaction 2 (RXN 2). In the case of cross-metathesis of 2-butene and 1-butene, the redistribution of these carbon-carbon double bonds through metathesis may produce propene and $C_5$-$C_6$ olefins.

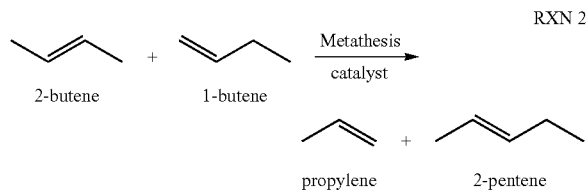

RXN 2

Further, as shown in the following Chemical Reaction 3 (RXN 3), "cracking" refers to the catalytic conversion of $C_4$-$C_6$ alkenes to propene and other alkanes, alkenes, or alkanes and alkenes, for example, $C_1$-$C_2$ alkenes. Catalytic conversion of $C_4$-$C_6$ alkenes to propene and other alkanes, alkenes, or alkanes and alkenes may further increase the yield of propene and ethylene from the metathesis system 130.

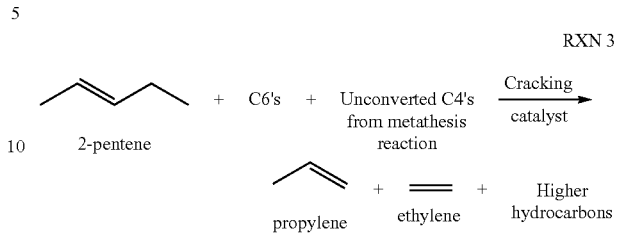

RXN 3

Referring to Chemical Reactions RXN 1-RXN 3, the metathesis and cracking reactions are not limited to these reactants and products; however, Chemical Reactions RXN 1-RXN 3 provide a simplified illustration of the reaction methodology.

The metathesis feed 142 passed to the metathesis system 130 may be any composition or stream comprising butenes, such as 1-butene, cis-2-butene, trans-2-butene, or combinations of these isomers. The metathesis feed 142 may also include other C4 hydrocarbons, such as butadiene, isobutene, n-butane, iso-butane, or combinations of these. The metathesis feed 142 may include some C5+ hydrocarbons, such as those produced or passed through the HS-FCC system 110. The metathesis feed 142 may include at least a portion of the cracking C4 effluent 112 from the HS-FCC system 110. Referring again to FIG. 1, in one or more embodiments, the cracking C4 effluent 112 may be passed directly from the HS-FCC system 110 to the metathesis system 130. Referring now to FIG. 4, in one or more embodiments, the cracking C4 effluent 112 may be passed to one or more unit operations, such as the isobutene removal unit 150, upstream of the metathesis system 130 so that only a portion of the cracking C4 effluent 112 is passed to the metathesis system 130 as the metathesis feed 142.

Referring again to FIG. 3, the metathesis feed 142 may include from 10 weight percent (wt. %) to 70 wt. %, from 10 wt. % to 60 wt. %, from 10 wt. % to 50 wt. %, from 20 wt. % to 70 wt. %, from 20 wt. % to 60 wt. %, or from 20 wt. % to 50 wt. % 2-butene based on the total weight of the metathesis feed 142. The metathesis feed 142 may include from 5 wt. % to 60 wt. %, from 5 wt. % to 50 wt. %, from 10 wt. % to 60 wt. %, from 10 wt. % to 50 wt. %, from 10 wt. % to 40 wt. %, from 15 wt. % to 60 wt. %, from 15 wt. % to 50 wt. %, or from 15 wt. % to 40 wt. % 1-butene based on the total weight of the metathesis feed 142. The metathesis feed 142 may include from 5 wt. % to 30 wt. % or 10 wt. % to 25 wt. % n-butane based on the total weight of the metathesis feed 142. The metathesis feed 142 may also include one or a plurality of ethylene, propene, isobutane, butadiene, isobutene, C5+ hydrocarbons, or combinations of these.

In one or more embodiments, the metathesis feed 142 may be substantially free of ethylene. As used in the present disclosure, the term "substantially free" of a component means less than 1 weight percent (wt. %) of that component in a particular portion of a catalyst, stream, or reaction zone. As a non-limiting example, a metathesis feed 142 that is substantially free of ethylene, may have less than 1 wt. % of ethylene based on the total weight of the metathesis feed 142. In one or more embodiments, the metathesis feed 142 may be substantially free of propene. In one or more embodiments, the metathesis feed 142 may be substantially free of isobutene. In one or more embodiments, the metathesis feed 142 may have less than 1.0 wt. % isobutene, or even less than 0.1 wt. % of isobutene, based on the total weight of the metathesis feed 142.

Referring again to FIG. 3, the metathesis reactor 140 may include one or a plurality of reaction zones, such as but not limited to, a metathesis reaction zone 141, a cracking reaction zone 142, or a combination of both. The metathesis reactor 140 may include at least one fixed bed reactor operated in an upflow or a downflow configuration. Although depicted as a fixed bed reactor, the metathesis reactor 140 may be any other type of reactor suitable for conducting a metathesis reaction. In one or more embodiments, the metathesis reactor 140 may include a plurality of metathesis reactors operated in series or in parallel. The metathesis reactor 140 may include a plurality of catalyst beds, where each of the catalyst beds may be a separate reaction zone. Two or more of the plurality of catalyst beds or reaction zones may be disposed in a single reactor. In embodiments, metathesis reactor 140 may include a single reactor having the metathesis reaction zone 141 comprising the metathesis catalyst and the cracking reaction zone 142 comprising the cracking catalyst and disposed downstream of the metathesis reaction zone 141.

In embodiments, the metathesis reactor 140 may include a plurality of catalyst beds or reaction zones where at least one of the catalyst beds or reaction zones is disposed in a separate reactor from the other of the plurality of catalyst beds or reaction zones. For example, the metathesis reactor 140 may include a first reactor (not shown) comprising the metathesis reaction zone 141 having the metathesis catalyst and a second reactor (not shown) disposed downstream of the first reactor and comprising the cracking reaction zone 142 that includes the cracking catalyst. The first reactor and the second reactor may be fluidly coupled by a conduit extending directly from the first reactor to the second reactor. The conduit may fluidly couple the first reactor and the second reactor in series.

The metathesis reactor 140 may be operable to contact the metathesis feed 142 with one or a plurality of catalysts, such as but not limited to the metathesis catalyst, a cracking catalyst, or both. In embodiments, the metathesis reactor 140 may include the metathesis reaction zone 141 and the cracking reaction zone 143 downstream of the metathesis reaction zone 141. The metathesis reaction zone 141 may include the metathesis catalyst, and the cracking reaction zone 143 may include the cracking catalyst. The metathesis feed 142 introduced to the metathesis reactor 140 may encounter the metathesis catalyst in the metathesis reaction zone 141 before encountering the cracking catalyst in the cracking reaction zone 143 downstream of the metathesis reaction zone 141.

Contacting of the metathesis feed 142 with the metathesis catalyst may cause at least a portion of the butene in the metathesis feed 142 to undergo a metathesis reaction to produce a metathesis reaction product that includes at least propene. The metathesis catalyst may be any catalyst operable to promote cross-metathesis of butenes to produce propene. The metathesis catalyst may be a particulate catalyst that includes a metal oxide disposed on the surfaces of a catalyst support material. The catalyst support material may be mesoporous silica catalyst support, such as but not limited to one or more molecular sieves or zeolites. As used in the present disclosure, "mesoporous" refers to a material having an average pore size of greater than 2 nanometers and less than 50 nanometers. The mesoporous silica catalyst support may include alumina or may be substantially free of alumina. As a non-limiting example, a mesoporous silica catalyst support that is substantially free of alumina may have less than 1 wt. % alumina.

The metathesis catalyst may include one or a plurality of metal oxides incorporated into the catalyst support material or deposited onto the surfaces of the catalyst support material. The metal oxide may include one or more oxides of a metal from Groups 6-10 of the IUPAC Periodic Table. As non-limiting examples, the metal oxide may include one or more oxides of molybdenum, rhenium, tungsten, or any combination of these. In one or more embodiments, the metal oxide of the metathesis catalyst may be tungsten oxide ($WO_3$). It is contemplated that various amounts of the metal oxide may be impregnated into the mesoporous silica catalyst support. For example and not by way of limitation, the weight percentage (wt. %) of metal oxide, for example $WO_3$, in the metathesis catalyst may be from 1 wt. % to 30 wt. %, such as from 5 wt. % to 25 wt. %, or even from 8 wt. % to 20 wt. % based on the total weight of the metathesis catalyst. The metal oxide may be incorporated into the catalyst support material through co-precipitation, methods, sol-gel methods, or other methods. Alternatively or additionally, the metal oxide may be deposited onto the outer surfaces and pore surfaces of the catalyst support material through any type of impregnation or deposition process, such as but not limited to wet impregnation, vapor deposition, or other suitable methods. The amount of metal oxide impregnated onto the catalyst support material of the metathesis catalyst may be verified using inductively coupled plasma (ICP) mass spectrometer or an x-ray fluorescence (XRF) spectrometer to determine the amount of tungsten in a sample of the mesoporous silica catalyst support impregnated with tungsten oxide.

The average pore size of the metathesis catalyst may be obtained from the average surface area and pore size distribution, which are determined using the Brunauer-Emmett-Teller (BET) method according to standard test methods known in the art. Average pore size is generally determined as a pore diameter or pore radius based on the assumption of cylindrical shaped pores. However, it is understood that metathesis catalysts described in this disclosure may have actual shapes that are cylindrical or other shapes, such as, but not limited to, conical, square, slit-shaped, or other irregular shaped pores or combinations of these. The metathesis catalyst may have a relative pore volume per weight of material of at least 0.6 cubic centimeters per gram ($cm^3/g$), such as from 0.6 $cm^3/g$ to 2.5 $cm^3/g$ or even from 0.7 $cm^3/g$ to 1.5 $cm^3/g$. The metathesis catalyst may have a surface area per unit weight of the metathesis catalyst of from 200 meters squared per gram ($m^2/g$) to 600 $m^2/g$, such as from 225 $m^2/g$ to 350 $m^2/g$, or even from 250 $m^2/g$ to 325 $m^2/g$. The metathesis catalyst may have a mean particle size of from 20 nanometers (nm) to 200 nm, such as from 50 nm to 150 nm. The metathesis catalyst may have a mean particle size distribution of from 100 angstroms (Å) to 300 A. The mean particle size and mean particle size distribution can be measured using a particle size analyzer, such as a Nanopartica™ series particle size analyzer from Horiba Scientific Company, which measures the size of single particles dispersed in water using ultraviolet (UV) light.

The metathesis catalyst may have a total acidity from 0.001 millimole/gram (mmol/g) to 0.5 mmol/g, from 0.01 mmol/g to 0.5 mmol/g, from 0.1 mmol/g to 0.5 mmol/g, from 0.3 mmol/g to 0.5 mmol/g, from 0.4 mmol/g to 0.5 mmol/g, from 0.001 mmol/g to 4 mmol/g, or from 0.001 mmol/g to 0.3 mmol/g. The acidity of the metathesis catalyst may be generally maintained at or less than 0.5 mmol/g to yield the desired propene selectivity of the multiple-stage catalyst system and to reduce production of undesirable byproducts, such as aromatics. Increasing acidity may increase the overall butene conversion; however, this increased conversion may lead to decreased propene selectivity and increased production of aromatic byproducts, which may lead to catalyst coking and deactivation.

Contact of the metathesis feed 142 with the metathesis catalyst in the metathesis reaction zone 141 may produce a metathesis reaction zone product that may include propene and other alkanes and alkenes, such as propene and other $C_5+$ olefins, for example. The metathesis reaction zone product may also include unreacted butenes, such as cis-2-butene, trans-2-butene, 1-butene, or combinations of two or more of these butenes. The metathesis catalyst may also promote self-metathesis of 2-butene to 1-butene, or 1-butene to 2-butene, in the metathesis reaction zone 141.

Referring again to FIG. 3, the metathesis reaction zone product may pass into contact with the cracking catalyst in the cracking reaction zone 143, which may be downstream of the metathesis reaction zone 141. The cracking reaction zone 143 may include a cracking catalyst capable of converting at least a portion of the unreacted 2-butene and the produced $C_5+$ olefins in the metathesis reaction zone product stream, to lighter olefins, such as ethylene and propene. Contact of the metathesis reaction zone product with the cracking catalyst in the cracking reaction zone 143 may cause at least a portion of the $C_5+$ olefins to undergo cracking to produce ethylene, propene, other lesser molecular weight olefins, or combinations of these.

The cracking catalyst may be any catalyst capable of catalyzing the cracking of $C_5+$ olefins to produce additional propene, ethylene, or both. The cracking catalyst may be a zeolite. In embodiments, the cracking catalyst may be a structured zeolite, such as MFI or BEA structured zeolite, for example. The cracking catalyst may be an MCM-41 catalyst or an SBA-15 catalyst. The cracking catalyst may be an MFI structured silica catalyst. For example, the MFI structured silica-containing catalyst may include MFI structured aluminosilicate zeolite catalysts or MFI structured silica catalysts that do not contain alumina or are substantially free of alumina, such as having less than 0.01 wt. % alumina based on the total weight of the catalyst. The cracking catalyst may be a MFI structured silica-containing catalyst which may include other impregnated metal oxides in addition to or as an alternative to alumina. The cracking catalyst may include one or more of the metal oxides of a metal from Groups 6-10 of the IUPAC Periodic Table, more specifically, metal oxides of molybdenum, rhenium, tungsten, titanium, or combinations of these. It should be understood that the cracking catalyst may include a combination of multiple zeolites, such as zeolite particles which include multiple types of zeolites, or a mixture of zeolite particles where particles include different zeolites. The cracking catalyst may be an MFI structured aluminosilicate zeolite catalyst which may have a molar ratio of silica to alumina of from 5 to 5000. Various suitable commercial embodiments of cracking catalyst comprising MFI structured aluminosilicate zeolites are contemplated, for example, ZSM-5 zeolites such as MFI-280 produced by Zeolyst International or MFI-2000 produced by Saudi Aramco. Various suitable commercial embodiments are also contemplated for the alumina free MFI structured silica-containing catalysts. One such example is Silicalite-1 produced by Saudi Aramco.

The cracking catalyst may have an average pore size of from 1.5 nm to 3 nm, or from 1.5 nm to 2.5 nm. The cracking catalyst may have an average relative pore volume per weight of material of from 0.1 $cm^3/g$ to 0.3 $cm^3/g$, or from 0.15 $cm^3/g$ to 0.25 $cm^3/g$. The cracking catalyst may have an average surface area of from 300 $m^2/g$ to 425 $m^2/g$, or from 340 $m^2/g$ to 410 $m^2/g$. The cracking catalyst may have an individual crystal size of from 10 microns to 40 microns, from 15 microns to 40 microns, or from 20 microns to 30 microns. The cracking catalyst may have a total acidity of from 0.001 mmol/g to 0.1 mmol/g, or from 0.01 mmol/g to 0.08 mmol/g. The acidity may be maintained at or less than 0.1 mmol/g to reduce production of undesirable byproducts, such as aromatic compounds. Increasing acidity may increase the amount of cracking; however, this increased cracking may also lead to less selectivity and increased production of aromatic hydrocarbon byproducts, which may lead to catalyst coking and deactivation. In some cases, the cracking catalyst may be modified with an acidity modifier to adjust the level of acidity in the cracking catalyst. Examples of acidity modifiers may include, but are not limited to, rare earth modifiers, phosphorus modifiers, potassium modifiers, or combinations of each. Alternatively, the cracking catalysts may be substantially free of acidity modifiers, such as those selected from rare earth modifiers, phosphorus modifiers, potassium modifiers, or combinations of each.

The reaction zones of the metathesis reactor 140 may optionally include an isomerization zone (not shown) having an isomerization catalyst. The isomerization zone may be disposed upstream of the metathesis reaction zones 141 and the cracking reaction zone 143. In one or more embodiments, the isomerization zone may be in a separate reactor upstream of the metathesis reactor 140 and fluidly coupled to the metathesis reactor 140 such that the isomerization reaction products pass directly from the isomerization reaction zone to the metathesis reaction zone 141. In some embodiments, the isomerization reaction zone may be disposed within the metathesis reactor 140 and upstream of the metathesis reaction zone 141. As previously discussed, the metathesis reactor 140 may include an isomerization reaction zone, which may include an isomerization catalyst, such as but not limited to magnesium oxide (MgO). The isomerization catalyst may promote equilibration of the isomerization reaction of 2-butene in the metathesis feed 142 to 1-butene.

Referring again to FIG. 3, the metathesis feed 142 may be contacted with metathesis catalyst or the metathesis catalyst and cracking catalyst in the metathesis reactor 140 under conditions sufficient to promote the cross-metathesis of at least a portion of the mixed butenes in the metathesis feed 142 to produce propene. The metathesis feed 142 may be contacted with the metathesis catalyst or the metathesis catalyst and cracking catalyst at a gas hourly space velocity (GHSV) of from 10 per hour ($h^{-1}$) to 10,000 $h^{-1}$, such as from 100 $h^{-1}$ to 5000 $h^{-1}$, or from 300 h-1 to 2500 h-1. The metathesis feed 142 may be contacted with the metathesis catalyst or the metathesis catalyst and cracking catalyst in the metathesis reactor 140 at a temperature of from 200° C. to 600° C., such as from 300° C. to 550° C., or even from 350° C. to 500° C. The metathesis feed 142 may be contacted with the metathesis catalyst or the metathesis catalyst and cracking catalyst in the metathesis reactor 140 at a pressure of from 1 bar to 30 bar or from 2 bar to 20 bar. In one or more embodiments, the metathesis feed 142 may be contacted with the metathesis catalyst or the metathesis catalyst and cracking catalyst in the metathesis reactor 140 at atmospheric pressure.

Contact of the metathesis feed 142 with the metathesis catalyst in the metathesis reaction zone 141 may cause at least a portion of the butenes (1-butene, trans-2-butene, cis-2-butene) to undergo metathesis to produce a metathesis reaction zone product stream that includes at least propene. The metathesis reaction zone product stream may additionally include $C_5+$ olefins, ethylene, butenes, or combinations of these. The metathesis reaction zone product stream may be passed directly into contact with the cracking catalyst in the cracking reaction zone 143. Contact of metathesis reaction zone product stream with the cracking catalyst in the cracking reaction zone 143 may cause at least a portion of the $C_5+$ olefins to undergo catalytic cracking reactions to produce the metathesis reaction effluent 144, which may have a greater concentration of propene compared to the metathesis reaction zone product stream prior to contacting with the cracking catalyst. The metathesis reaction effluent 144 may be passed out of the metathesis reactor 140. The metathesis reaction effluent 144 may additionally include one or more of ethylene, unreacted butenes, fuel gas, propane, isobutane, n-butane, isobutene, butadiene, and C5+ compounds. At least a portion of the propane, n-butane, isobutane, isobutene, and butadiene in the metathesis reaction effluent 144 may be constituents that pass through the metathesis reactor 140 without undergoing reaction to form olefins. The ethylene and certain C5+ compounds, such as but not limited to pentene or hexene, may be produced in the metathesis reactor 140 through the metathesis reactions. At least a portion of the C5+ olefins may be converted to propene, ethylene, or olefins through contact with the cracking catalyst.

Referring again to FIG. 3, the metathesis reaction effluent 144 may be passed from the metathesis reactor 140 to the metathesis effluent separation system 146. The metathesis effluent separation system 146 may be fluidly coupled to the metathesis reactor 140 so that the metathesis reaction effluent 144 can be passed directly from the metathesis reactor 140 to the metathesis effluent separation system 146 without passing the metathesis reaction effluent 144 through any intervening unit operations, such as a reactor or intervening separation system. The metathesis effluent separation system 146 may include one or a plurality of separators operable to separate the metathesis reaction effluent 144 into at least a metathesis C5+ effluent 134 and at least one other olefin-containing effluent, which may include at least one of ethylene, propene, normal butenes, or combinations of these. In one or more embodiments, the metathesis C5+ effluent 134 and the at least one other olefin-containing effluent may comprise at least 95 percent by weight of the constituents of the metathesis reaction effluent 144. The metathesis effluent separation system 146 may be operable to separate the metathesis reaction effluent 144 into a metathesis C4 effluent 132, the metathesis C5+ effluent 134, a metathesis propene effluent 136, and a metathesis ethylene effluent 138. The metathesis C4 effluent 132, metathesis C5+ effluent 134, metathesis propene effluent 136, and metathesis ethylene effluent 138, combined, may include at least 95 percent by weight of the constituents of the metathesis reaction effluent 144. The separation units of the metathesis effluent separation system 146 may include, but are not limited to, flash drums, high-pressure separators, distillation units, fractional distillation units, membrane separation units, or combinations of these. One or more of the metathesis C4 effluent 132, metathesis C5+ effluent 134, the metathesis propene effluent 136, the metathesis ethylene effluent 138 may be passed to one or more downstream unit operations for further processing.

Referring now to FIG. 4, the metathesis C5+ effluent 134 may be passed from the metathesis system 130 back to the HS-FCC system 110, in which the metathesis C5+ effluent 134 can be contacted with the cracking catalyst under high-severity conditions to produce additional olefins, such as ethylene, propene, and butene. The metathesis C5+ effluent 134 may be passed directly to the HS-FCC system 110, such as directly to the mixing zone 210 (FIG. 2) of the HS-FCC system 110, or the metathesis C5+ effluent 134 may be combined with the hydrocarbon feed 102 upstream of the HS-FCC system 110 to produce a combined feed to the HS-FCC system 110. The system 100 may include a metathesis C5+ recycle 135 fluidly coupled to the metathesis system 130, such as to the metathesis effluent separation system 146 of the metathesis system 130, and to the HS-FCC system 110, such as to the mixing zone 210 of the HS-FCC system 110. The metathesis C5+ recycle 135 may be operable to pass the metathesis C5+ effluent 134 from the metathesis system 130 back to the HS-FCC system 110.

Contacting the C5+ compounds of the metathesis C5+ effluent 134 with the cracking catalyst under high-severity conditions in the HS-FCC system 110 may cause at least a portion of the C5+ compounds from the metathesis C5+ effluent 134 to undergo cracking reactions to produce olefins, such as ethylene, propene, and butene, and other C4– compounds. The additional conversion of at least a portion of the C5+ compounds from the metathesis C5+ effluent 134 may increase the overall conversion of the system 100 for producing olefins, such as ethylene and propene. Some portions of the C5+ compounds of the metathesis C5+ effluent 134 may undergo cracking in the HS-FCC system 110 to produce ethylene or propene, which may be passed out of the HS-FCC system 110 in the cracking ethylene effluent 117 and the cracking propene effluent 116, respectively. Additionally, other portions of the C5+ compounds from the metathesis C5+ effluent 134 may be converted to butenes through contact with the cracking catalyst. The butenes produced from cracking the portion of the C5+ compounds may be passed to the metathesis system 130 downstream of the HS-FCC system 110 for further conversion to ethylene and propene through metathesis. Thus, passing the metathesis C5+ effluent 134 containing the C5+ compounds produced in the metathesis system 130 back to the HS-FCC system 110 may increase the overall conversion of the hydrocarbon feed 102 and the overall yield of propene for the system 100.

Referring again to FIG. 4, the metathesis C4 effluent 132 may include one or more of n-butane, isobutane, unreacted normal butenes, butadiene, isobutene, or combinations of these. The metathesis C4 effluent 132 may also include other compounds having boiling point temperatures in the range of the C4 compounds of the metathesis C4 effluent 132, such as boiling point temperatures greater than the boiling point temperature of propene and less than the boiling point temperatures of the metathesis C5+ effluent 134. The metathesis C4 effluent 132 may be passed to one or a plurality of downstream unit operations (not shown) for further processing. Additionally or alternatively, the metathesis C4 effluent 132 may be recycled back to the metathesis reactor 140 of the metathesis system 130 for further conversion of a portion of the butenes in the metathesis C4 effluent 132 to ethylene and propene. The at least a portion of the metathesis C4 effluent 132 may be passed from the metathesis effluent separation system 146 directly back to the metathesis reactor 140 or may be combined with the metathesis feed 142 upstream of the metathesis reactor 140 to produce a combined metathesis feed stream. The system 100 may include a metathesis C4 effluent recycle 133, which may be fluidly coupled to an outlet of the metathesis effluent separation system 146 of the metathesis system 130 and an inlet of the metathesis reactor 140 of the metathesis system 130. The metathesis C4 effluent recycle 133 may be operable to transfer at least a portion of the metathesis C4 effluent 132 from the metathesis effluent separation system 146 back to the metathesis reactor 140 and into contact with the metathesis catalyst in the metathesis reactor 140.

Passing the metathesis C4 effluent 132 back to the metathesis reactor 140 and contacting the metathesis C4 effluent 132 with the metathesis catalyst in the metathesis reactor 140 may further increase the overall conversion and yield of ethylene and propene of the system 100. Contacting the metathesis C4 effluent 132 with the metathesis catalyst in the metathesis reactor 140 may cause at least a portion of the butenes in the metathesis C4 effluent 132 to undergo metathesis reactions to produce olefins, such as ethylene, propene, or both. Thus, recycling the metathesis C4 effluent 132 back to the metathesis reactor 140 and into contact with the metathesis catalyst may increase the overall conversion and yield of propene from the system 100. Recycling the metathesis C4 effluent 132 back to the metathesis reactor 140 and into contact with the metathesis catalyst may also increase the yield of ethylene from the system 100.

Referring to FIG. 4, the metathesis propene effluent 136 and the metathesis ethylene effluent 138 may be passed to one or more downstream unit operations for further processing, such as but not limited to purification or polymerization processes. The metathesis propene effluent 136 may be combined with the cracking propene effluent 116 from the HS-FCC system 110 to form a combined propene effluent from the system 100. Likewise, the metathesis ethylene effluent 138 may be combined with the cracking ethylene effluent 117 to form a combined ethylene effluent from the system 100. The combined propene effluent and the combined ethylene effluent from the system 100 may be passed independently to downstream operations for further processing.

In one or more embodiments, the metathesis ethylene effluent 138 may not be passed back to the metathesis reactor 140 and no supplemental ethylene may be introduced or passed to the metathesis reactor 140. Ethylene itself can be a valuable intermediate for producing other chemical products, such as polyethylene and other polymers. Thus, the metathesis reactor 140 may be operated in the absence of any supplemental ethylene introduced to the metathesis reactor 140 and the only ethylene present in the metathesis reactor 140 may be any residual ethylene incidentally remaining in the metathesis feed 142 passed from the HS-FCC system 110 to the metathesis system 130 and the ethylene produced in the metathesis reactor 140 through cross-metathesis of 1-butene and 2-butene.

As previously discussed, the cracking C4 effluent 112 from the HS-FCC system 110 may include isobutene, which may have a negative impact on the propene selectivity and yield of the system 100. Isobutene may undergo cross-metathesis with 1-butene or 2-butene. Cross-metathesis between isobutene and 2-butene produces propene and 2-methyl-2-propene, which is productive for producing propene. However, cross-metathesis between isobutene and 1-butene produces ethylene and 2-methyl-2-propene with no propene produced. Therefore, the presence of isobutene in the metathesis feed 142 may operate to reduce the selectivity and yield of propene from the system 100.

Referring again to FIG. 4, to further increase the selectivity and yield of propene, the system 100 may include the isobutene removal unit 150 disposed downstream of the HS-FCC system 110. The isobutene removal unit 150 may be disposed between the HS-FCC system 110 and the metathesis system 130 such that the isobutene removal unit 150 is downstream of the HS-FCC system 110 and the metathesis system 130 is downstream of the isobutene removal unit 150. The isobutene removal unit 150 may be operable to receive the cracking C4 effluent 112 from the HS-FCC system 110 and remove isobutene from the cracking C4 effluent 112 to produce the metathesis feed 142, which may have a decreased concentration of isobutene compared to the cracking C4 effluent 112. The isobutene removal unit 150 may include a methyl-tert-butyl ether reactor 170 (MTBE reactor 170), which may be operable to convert at least a portion of the isobutene to methyl-tert-butyl ether (MTBE).

Figure 5:
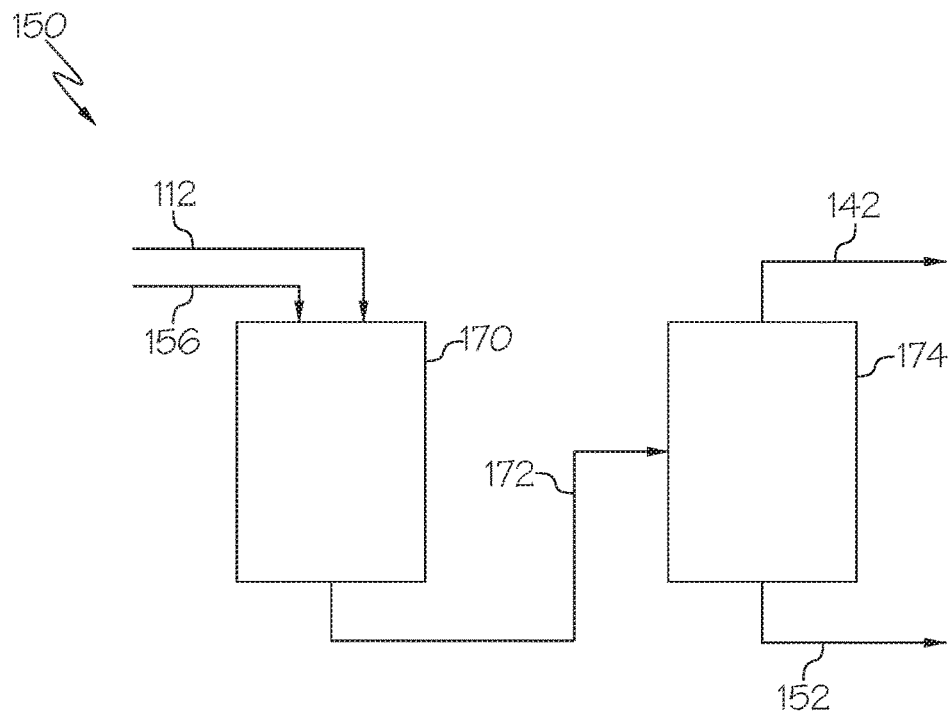
FIG. 5 schematically depicts a process flow diagram of the isobutene removal unit of the system of FIG. 4, according to one or more embodiments shown and described in the present disclosure.

Referring to FIG. 5, the isobutene removal system 150 may include the MTBE reactor 170 and an MTBE separation system 174 downstream of the MTBE reactor 170. MTBE reactor 170 may include a cation exchange resin or an acid catalyst. The MTBE reactor 170 may be operable to contact the cracking C4 effluent 112 and methanol from a methanol feed 156 in the presence of the cation exchange resin or acid catalyst at reaction conditions sufficient to convert at least a portion of the isobutene in the cracking C4 effluent 112 to MTBE. The MTBE reactor 170 may be operated at a temperature of from 35° C. to 100° C. Contacting the cracking C4 effluent 112 with the methanol in the presence of the cation exchange resin or acid catalyst in the MTBE reactor 170 may cause at least a portion of the isobutene in the cracking C4 effluent 112 to undergo etherification to produce MTBE.

An MTBE reactor effluent 172, which may include at least the MTBE, excess methanol, and the unreacted constituents of the cracking C4 effluent 112, may be passed to the MTBE separation system 174 downstream of the MTBE reactor 170. The MTBE reactor effluent 172 may include a concentration of isobutene less than the concentration of isobutene in the cracking C4 effluent 112. The MTBE separation system 174 may include one or a plurality of separation units operable to separate the MTBE reactor effluent 172 into at least the metathesis feed 142 and an MTBE-containing effluent 152. The metathesis feed 142 and the MTBE-containing effluent 152 may comprise at least 95 percent by weight of the constituents of the MTBE reactor effluent 172. The MTBE-containing effluent 152 may include at least 80%, at least 90%, at least 95%, or even at least 98% of the MTBE produced in the MTBE reactor 170. In one or more embodiments, the MTBE separation system 174 may also be operable to produce a methanol effluent comprising at least a portion of the excess methanol from the MTBE reaction, which may be recycled back to the MTBE reactor 170. Referring again to FIG. 4, the metathesis feed 142 may be passed to the metathesis system 130 downstream of the isobutene removal unit 150. The MTBE-containing effluent 152 may be passed out of the system 100 to one or more downstream unit operations for further processing.

Referring again to FIG. 5, in one or more embodiments, at least a portion of the MTBE-containing effluent 152 may be passed back to the HS-FCC system 110 through the MTBE recycle loop 154, which may be a conduit, pipe, or other flow path fluidly coupling the isobutene removal unit 150 to the inlet of the HS-FCC system 110. The MTBE recycle loop 154 may be operable to pass at least a portion of the MTBE-containing effluent 152 directly from the MTBE separation system 174 to the mixing zone 210 of the HS-FCC system 110. The MTBE recycle loop 154 may also be operable to pass the portion of the MTBE-containing effluent 152 into combination with the hydrocarbon feed 102, metathesis C5+ effluent 134, or both, upstream of the mixing zone 210. The at least a portion of the MTBE-containing effluent 152 passed back to the HS-FCC system 110 may be contacted with the cracking catalyst at high-severity conditions. Contacting the portion of the MTBE-containing effluent 152 with the cracking catalyst at high-severity conditions may cause at least a portion of the MTBE and other organic constituents that may be in the MTBE-containing effluent 152 to undergo cracking reactions to form one or more different organic compounds, such as but not limited to olefins. Some of the MTBE may be converted to olefins, such as but not limited to, ethylene, propene, butene, or combinations of these. Thus, passing at least a portion of the MTBE-containing effluent 152 back to the HS-FCC system 110 through the MTBE recycle loop 154 may increase the overall conversion and propene selectivity and yield of the system 100 compared to removing all of the MTBE-containing effluent 152 from the system 100.

Referring again to FIG. 4, the metathesis C4 effluent 132 passed out of the metathesis system 130 may also include isobutene. In one or more embodiments, at least a portion of the metathesis C4 effluent 132 may be passed to the isobutene removal unit 150 so that at least a portion of the isobutene in the metathesis C4 effluent 132 can be removed through reaction with methanol to produce MTBE. The portion of the metathesis C4 effluent 132 may be passed back to the isobutene removal unit 150 as the metathesis C4 effluent recycle 133. The metathesis C4 effluent recycle 133 may be passed directly to the isobutene removal unit 150, such as directly to the MTBE reactor 170 of the isobutene removal unit 150, or may be combined with the cracking C4 effluent 112 upstream of the isobutene removal unit 150. Recycling at least a portion of the metathesis C4 effluent 132 back to the isobutene removal unit 150 as the metathesis C4 effluent recycle 133 may further increase the selectivity and yield of propene for the system 100 by removing isobutene from the metathesis C4 effluent 132 before passing it back to the metathesis system 130.

Figure 6:
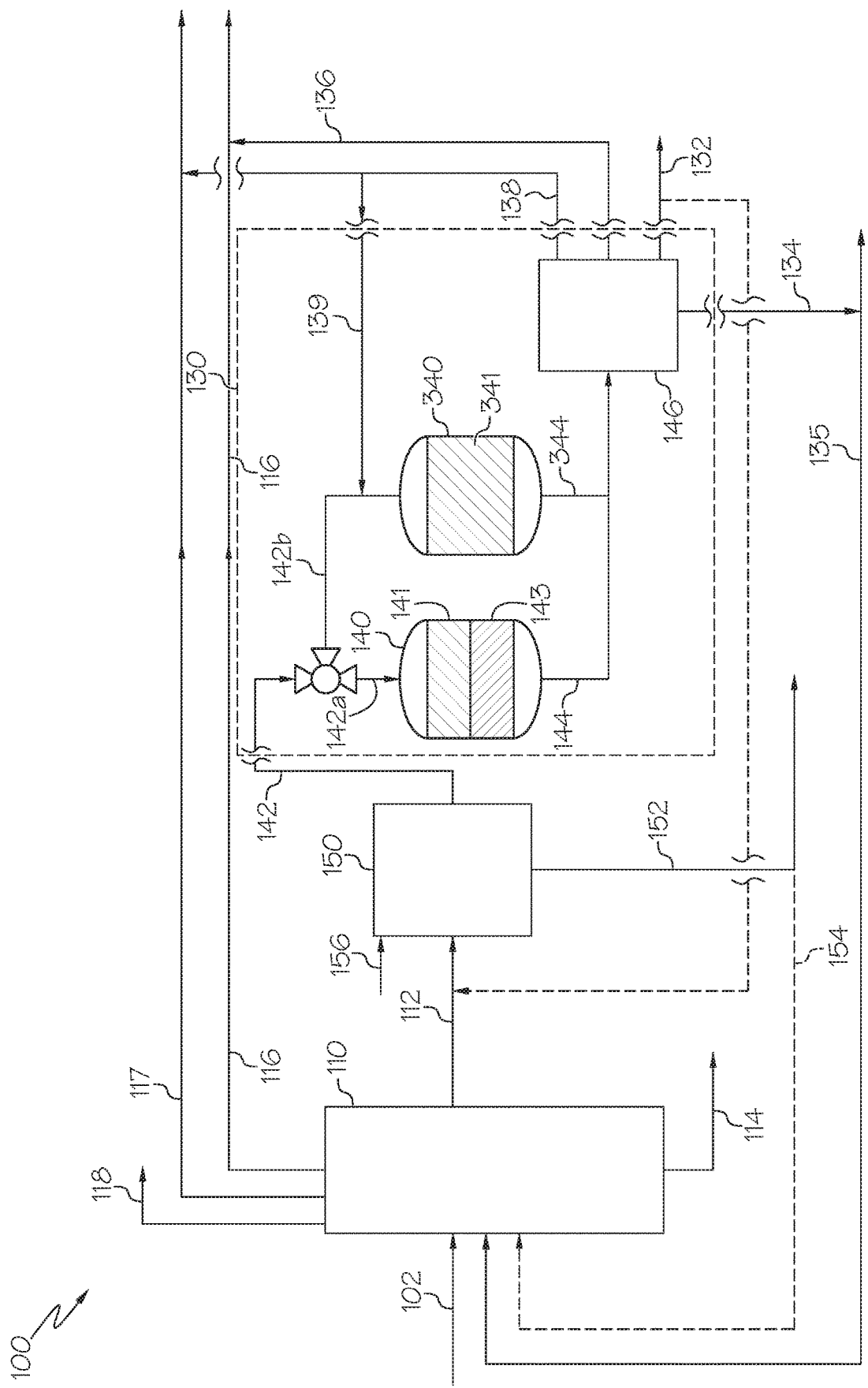
FIG. 6 schematically depicts a process flow diagram of another system for producing olefins, according to one or more embodiments shown and described in the present disclosure.

Referring now to FIG. 6, ethylene produced through metathesis of butene in the metathesis system 130 may be recycled back to the metathesis system 130 as a reactant. In the metathesis system 130, the ethylene may react with 2-butene in the presence of the metathesis catalyst to produce propylene. When ethylene is recycled back to the metathesis system 130, the metathesis system 130 may include the metathesis reactor 140 and a supplemental metathesis reactor 340, which may be operated in parallel with the metathesis reactor 140. The metathesis reactor 140 may include the metathesis reaction zone 141 with the metathesis catalyst and the cracking reaction zone 143 with the cracking catalyst downstream of the metathesis reaction zone 141. The metathesis reactor 140 may have any of the features, catalysts, or operating conditions previously described in the present disclosure for the metathesis reactor 140.

Referring to FIG. 6, the supplemental metathesis reactor 340 may include at least one metathesis reaction zone 341 comprising a supplemental metathesis catalyst. The supplemental metathesis catalyst in the supplemental metathesis reactor 340 may be the same as or different from the metathesis catalyst in the metathesis reaction zone 141 of the metathesis reactor 140. The supplemental metathesis catalyst in the supplemental metathesis reactor 340 may have any of features, compositions, or characteristics previously described in the present disclosure for the metathesis catalyst. The supplemental metathesis reactor 340 may include one or a plurality of metathesis reaction zones 341 operated in series or in parallel. In embodiments, the supplemental metathesis reactor 340 may not include a cracking catalyst. In embodiments, the supplemental metathesis reactor 340 may include an isomerization catalyst operable to isomerize 1-butene to 2-butene.

Referring to FIG. 6, a first portion 142a of the metathesis feed 142 may be directed to the metathesis reactor 140 and a second portion 142b of the metathesis feed 142 may be directed to the supplemental metathesis reactor 340. The first portion 142a of the metathesis feed 142 may be contacted with the metathesis catalyst in the metathesis reaction zone 141 and the cracking catalyst in the cracking reaction zone 143 to produce the metathesis reaction effluent 144. The second portion 142b of the metathesis feed 142 may be passed to the supplemental metathesis reactor 340. At least a portion of the metathesis ethylene effluent 138 may also be passed to the supplemental metathesis reactor 340. The portion of the metathesis ethylene effluent 138 may be passed to the supplemental metathesis reactor 340 through a metathesis ethylene recycle 139. The metathesis ethylene recycle 139 may be operable to pass at least a portion of the metathesis ethylene effluent 138 from the metathesis effluent separation system 146 back to the supplemental metathesis reactor 340. The metathesis ethylene recycle 139 may be combined with the second portion 142b of the metathesis feed 142 upstream of the supplemental metathesis reactor 340 or may be passed to the supplemental metathesis reactor 340 independent of the second portion 142b of the metathesis feed 142.

Referring to FIG. 6, the second portion 142b of the metathesis feed 142 and the ethylene from the metathesis ethylene recycle 139 may be combined in the supplemental metathesis reactor 340 and contacted with the supplemental metathesis catalyst in the metathesis reaction zone 341. Contact between the ethylene and 2-butene (trans-2-butene, cis-2-butene, or both) in the presence of the supplemental metathesis catalyst in the metathesis catalyst zone 341 may cause cross-metathesis between at least a portion of ethylene from the metathesis ethylene recycle 139 and the 2-butenes from the second portion 142b of the metathesis feed 142 to produce propene. Cross-metathesis between 1-butene and 2-butene to produce propene and pentene and other metathesis reactions may also occur in the supplemental metathesis reactor 340. A supplemental metathesis reaction effluent 344 may be passed out of the supplemental metathesis reactor 340. The supplemental metathesis reaction effluent 344 may include the propene, ethylene, and C5+ olefins produced through the various cross-metathesis reactions occurring in the supplemental metathesis reactor 340 as well as unreacted ethylene and C4 constituents from the second portion 142b of the metathesis feed 142.

Recycling at least a portion of the metathesis ethylene effluent 138 back to the metathesis system 130 through the metathesis ethylene recycle 139 may operate to shift the system 100 towards greater yield of propene relative to ethylene compared to operation of the system 100 without recycling the metathesis ethylene effluent 138 back to the metathesis system 130. Thus, recycling at least a portion of the metathesis ethylene effluent 138 back to the metathesis system 130 may further increase the selectivity and yield of propene from the system 100.

Referring again to FIG. 6, the metathesis reaction effluent 144 and the supplemental metathesis reaction effluent 344 may be passed to the metathesis effluent separation system 146. The metathesis reaction effluent 144 and the supplemental metathesis reaction effluent 344 may be passed individually to the metathesis effluent separation system 146 or may be combined upstream of the metathesis effluent separation system 146. As previously discussed, the metathesis effluent separation system 146 may be operable to separate the metathesis reaction effluents into a plurality of effluent streams, such as but not limited to the metathesis C4 effluent, the metathesis C5+ effluent, the metathesis propene effluent 136, and the metathesis ethylene effluent 138. As previously discussed, at least a portion of the metathesis C5+ effluent 134 may be passed back to the HS-FCC system 110 through the metathesis C5+ recycle 135, and at least a portion of the metathesis C4 effluent 132 may be passed back to the isobutene removal unit 150.

Referring now to FIG. 7, the system 100 may not include the metathesis effluent separation system 146. Instead, the system 100 may include a combined separation system 300, and the metathesis reaction effluent 144 and the cracking reaction effluent 232 may both be passed to the combined separation system 300. The metathesis reaction effluent 144 and the cracking reaction effluent 232 may be passed separately and independently to the combined separation system 300 or may be combined upstream of the combined separation system 300. The combined separation system 300 may include one or a plurality of separation units in series or in parallel. The combined separation system 300 may be operable to separate the metathesis reaction effluent 144 and the cracking reaction effluent 232 into at least a C4 stream 312, a greater boiling effluent 314, a propene effluent 316, an ethylene effluent 317, and a lesser-molecular weight gas effluent 318. The metathesis reaction effluent 144 may be passed directly from the metathesis reactor 140 to the combined separation system 300. Although not depicted in FIG. 7, at least a portion of the greater boiling effluent 314 may be passed back to the HS-FCC reactor unit 200.

The metathesis reaction effluent 144 may include isobutene produced in the metathesis reactor 140. This isobutene may pass out of the combined separation system 300 in the C4 stream 312. The C4 stream 312 may then be passed to the isobutene removal unit 150 so that at least a portion of the isobutene from the metathesis reaction effluent 144 can be removed through reaction with methanol to produce MTBE. At least a portion of the MTBE-containing effluent 152 may be passed from the isobutene removal unit 150 back to the HS-FCC system 110 through the MTBE recycle loop 154. The combined separation system 300 may also be used in the system 100 in which the ethylene is recycled back to the metathesis reaction system 130 as shown in FIG. 6.

Referring again to FIG. 4, processes for producing olefins may be conducted using the systems 100 of the present disclosure, which may include the HS-FCC system 110, the metathesis system 130, and the isobutene removal unit 150 previously described in the present disclosure. The process may include contacting the hydrocarbon feed 102 with a cracking catalyst under high-severity conditions to produce a cracking reaction effluent 232 comprising at least butene. The high-severity conditions may include a temperature of greater than or equal to 500° C., a residence time of less than 3 seconds, and a cracking catalyst to hydrocarbon weight ratio of greater than 5:1. Contacting the hydrocarbon feed 102 with the cracking catalyst may be conducted at a temperature of from 500° C. to 800° C., for a residence time of from 0.2 seconds to 3 seconds, and at a cracking catalyst to hydrocarbon weight ratio of from 5:1 to 40:1. The process may further include contacting at least a portion of the butene from the cracking reaction effluent 232 with a metathesis catalyst. Contacting of the butene from the cracking reaction effluent 232 with the metathesis catalyst may cause metathesis of at least a portion of the butene to produce a metathesis reaction effluent 144. The process may include contacting at least a portion of the butene from the cracking reaction effluent 232 with a metathesis catalyst and a cracking catalyst downstream of the metathesis catalyst, where contact with the cracking catalyst may further convert C4+ olefins to ethylene, propene, or other lesser molecular weight hydrocarbons. The process may further include separating the metathesis reaction effluent 144 into a metathesis C5+ effluent 134 and at least one olefin-containing effluent. The at least one olefin-containing effluent may include at least one of ethylene, propene, or butene. The method may further include contacting at least a portion of the metathesis C5+ effluent 134 with the cracking catalyst and the hydrocarbon feed 102 under high-severity conditions to produce the cracking reaction effluent 232. The process for producing olefins may include separating the cracking reaction effluent 232 into a cracking C4 effluent 112 and at least one other effluent stream, where the cracking C4 effluent 112 comprises butene, and passing only the cracking C4 effluent 112 into contact with the metathesis catalyst.

The hydrocarbon feed 102 may include naphtha, a gas condensate, or both. The cracking reaction effluent 232, the cracking C4 effluent 112, or both, may include isobutene, and the process may further include removing isobutene from the cracking reaction effluent 232 or the cracking C4 effluent 112 to produce the metathesis feed 142. The metathesis feed 142 may be substantially free of isobutene. Removing isobutene from the cracking reaction effluent 232 or the cracking C4 effluent 112 to produce the metathesis feed 142 may include contacting the cracking reaction effluent 232 with methanol under reaction conditions sufficient to convert at least a portion of the isobutene to methyl tert-butyl ether to produce an MTBE reaction product 172. Removing the isobutene may further include separating at least a portion of the methyl tert-butyl ether from the MTBE reaction product 172 to produce an MTBE-containing effluent 152 comprising the methyl tert-butyl ether and a metathesis feed 142 comprising butene. The process may further include contacting the methyl tert-butyl ether with the cracking catalyst and the hydrocarbon feed 102 under high-severity conditions to produce the cracking reaction effluent 232.

The process for producing olefins may further include separating the metathesis reaction effluent 144 into the metathesis C5+ effluent 134, the metathesis C4 effluent 132, the metathesis propene effluent 136, and the metathesis ethylene effluent 138. After separation of the metathesis reaction effluent 144, the process for producing olefins may include passing at least a portion of the metathesis C4 effluent 132 back into contact with the metathesis catalyst or the metathesis catalyst and cracking catalyst, where the contact causes further metathesis of butene in the metathesis C4 effluent 134 to produce the metathesis reaction effluent 144. The process may further include passing at least a portion of the metathesis ethylene effluent 138 back into contact with the metathesis catalyst. In one or more embodiments, the ethylene effluent 138 may not be passed back into contact with the metathesis catalyst and no supplemental ethylene may be introduced into contact with the metathesis catalyst. Referring to FIG. 6, in embodiments, the process may include contacting a first portion 142a of the metathesis feed 142 with a metathesis catalyst and a cracking catalyst in the metathesis reactor 140 to produce the metathesis reaction effluent 144 and contacting a second portion 142b of the metathesis feed 142 and at least a portion of the metathesis ethylene effluent 138 with a supplemental metathesis catalyst in a supplemental metathesis reactor 340 to produce a supplemental metathesis reaction effluent 344. The metathesis reaction effluent 144 and the supplemental metathesis reaction effluent 344 may be combined and separated into the plurality of metathesis effluent streams.

Referring again to FIG. 4, in one or more embodiments, the processes for producing olefins may include introducing the hydrocarbon feed 102 to the HS-FCC system 110 and contacting the hydrocarbon feed 102 with a cracking catalyst under high-severity conditions in the HS-FCC system 110 to produce at least a cracking C4 effluent 112 comprising butene. The high-severity conditions may include a temperature of greater than or equal to 500° C., a residence time of less than or equal to 3 seconds, and a weight ratio of the cracking catalyst to hydrocarbon of 5:1. Contacting the hydrocarbon feed 102 with the cracking catalyst may be conducted in the HS-FCC reactor 220 of the HS-FCC system 110 at a temperature of from 500° C. to 800° C., for a residence time of from 0.2 seconds to 3 seconds, and at a cracking catalyst to hydrocarbon weight ratio of from 5:1 to 40:1. The process may further include passing at least a portion of the cracking C4 effluent 112 to the metathesis system 130 and contacting the portion of the cracking C4 effluent 112 with a metathesis catalyst in the metathesis system 130. Contacting the portion of the cracking C4 effluent 112 with the metathesis catalyst may cause at least a portion of butene in the cracking C4 effluent 112 to undergo metathesis to produce a metathesis effluent 144 comprising at least one of ethylene, propene, or both. The process may include contacting at least a portion of the cracking C4 effluent 112 with the metathesis catalyst in a metathesis reaction zone 141 and a cracking catalyst in a cracking reaction zone 143 downstream of the metathesis reaction zone 141, where contact with the cracking catalyst may further convert C4+ olefins to ethylene, propene, or other lesser molecular weight hydrocarbons. The process may include separating the metathesis C5+ effluent 134 from the metathesis effluent 144 and passing the metathesis C5+ effluent 134 to the HS-FCC system 110. The HS-FCC system 110 and metathesis system 130 may have any of the features, operating conditions, or characteristics previously described in the present disclosure for the HS-FCC system 110 and the metathesis system 130.

The hydrocarbon feed 102 may be a naphtha stream, a gas condensate stream, or both. The cracking C4 effluent 112 may include isobutene, and the processes for producing olefins may further include passing at least a portion of the cracking C4 effluent 112 to an isobutene removal unit 150. The isobutene removal unit 150 may have any of the features, operating conditions, or characteristics previously described in this disclosure for the isobutene removal unit 150. The process for producing olefins may further include contacting the isobutene in the cracking C4 effluent 112 with methanol in an MTBE reactor 170 of the isobutene removal unit 150 under reaction conditions sufficient to convert at least a portion of the isobutene in the cracking C4 effluent 112 to methyl tert-butyl ether to produce an MTBE reactor effluent 172, separating the MTBE reactor effluent 172 into at least an MTBE-containing effluent 152 and a metathesis feed 142, and passing the metathesis feed 142 to the metathesis system 130. The metathesis feed 142 may include at least butenes, such as 1-butene, trans-2-butene, cis-2-butene, or combinations of these. The process for producing olefins may further include passing at least a portion of the MTBE-containing effluent 152 back to the HS-FCC system 110.

The process for producing olefins may further include separating the metathesis effluent 144 into the metathesis C4 effluent 132, the metathesis C5+ effluent 134, the metathesis propene effluent 136, and the metathesis ethylene effluent 138. The process for producing olefins may further include passing at least a portion of the metathesis C4 effluent 132 back to the metathesis system 130 or the isobutene removal unit 150 upstream of the metathesis system 130. The process for producing olefins may further include passing at least a portion of the metathesis ethylene effluent 138 back to the metathesis system 130 or to the isobutene removal unit 150 upstream of the metathesis system 130. In one or more embodiments, the metathesis ethylene effluent 138 may not be passed to the metathesis system 130 and no supplemental ethylene may be introduced to the metathesis system 130. Referring to FIG. 6, in embodiments, the process may include contacting a first portion 142a of the metathesis feed 142 with a metathesis catalyst and a cracking catalyst in the metathesis reactor 140 to produce the metathesis reaction effluent 144 and contacting a second portion 142b of the metathesis feed 142 and at least a portion of the metathesis ethylene effluent 138 with a supplemental metathesis catalyst in a supplemental metathesis reactor 340 to produce a supplemental metathesis reaction effluent 344. The metathesis reaction effluent 144 and the supplemental metathesis reaction effluent 344 may be combined and separated into the plurality of metathesis effluent streams.

Contacting the hydrocarbon feed 102 with the cracking catalyst in the HS-FCC system 110 may produce a cracking reaction effluent 232, and the process for producing olefins may further include separating the cracking reaction effluent 232 into the cracking C4 effluent 112 comprising butene and at least one other effluent stream. Separating the cracking reaction effluent 232 may include passing the cracking reaction effluent 232 to a cracking effluent separation system 250 (FIG. 2) that may include one or a plurality of separators operable to separate the cracking reaction effluent 232 into the cracking C4 effluent 112 and at least one of a cracking propene effluent 116, a cracking ethylene effluent 117, a lesser-molecular weight gas effluent 118, a greater-boiling temperature effluent 114, or combinations of these.

The systems and processes of the present disclosure may be employed to produce olefins, such as ethylene and propene, from hydrocarbon feeds, such as naphtha and gas condensate streams. The ethylene and propene produced by the systems and processes of the present disclosure may be used as intermediates in various chemical processes to produce further valuable chemical products. As a non-limiting example, the ethylene and propene may be introduced to a polymerization process to make polymer materials, such as but not limited to polyethylene-based polymers, polypropene-based polymers, or combinations of these. Ethylene and propene may also be used as reactants in various other reactions, such as but not limited to, oxidation, alkylation, oligomerization, hydration, to produce valuable chemical products. Other known uses of the ethylene and propene produced by the systems and processes of the present disclosure are also contemplated.

EXAMPLES

The following non-limiting examples illustrate one or more features of the present disclosure.

Example 1: Cracking Reaction Products from High-Severity Fluidized Catalytic Cracking of a Naphtha Feed In Example 1, the composition of the cracking reaction products resulting from contacting a naphtha feed with a cracking catalyst under high-severity conditions was determined. The naphtha feed was an Arab Extra Light naphtha stream produced by Saudi Arabian Oil Company. The HS-FCC process included an AmTech Microdowner reactor system comprising a zeolite cracking catalyst. The zeolite cracking catalyst was an equilibrium catalyst (Ecat) from Grace Davidson combined with up to 25 wt. % OlefinMax additive. The fluidized cracking reactor of the HS-FCC process was operated under high-severity conditions, which included a reaction temperature of 650° C., a catalyst to hydrocarbon ratio of from 15:1 to 30:1, and a residence time of from 0.5 seconds to 1.25 seconds. The HS-FCC process was operated at a pressure of from 75 kilopascals (kPa) to 150 kPa. Steam was added to the feed upstream of the fluidized cracking reactor. Contact of the naphtha feed with the cracking catalyst at the reaction conditions produced a cracking reaction product having the composition in Table 2.

TABLE 2

Cracking reaction products from high-severity fluidized catalytic cracking of a naphtha feed for Example 1

| Feed | Cracking Reaction Product from Naphtha Feed | |
| --- | --- | --- |
| Product Yields | wt. % | Ktpa |
| Fuel Gas | 3.9 | 107 |
| Ethylene | 5.1 | 140 |
| Propene | 14.2 | 390 |
| Propane | 1.6 | 45 |
| Mixed C4 Compounds | 13.2 | 362 |
| 95 RON (10 ppmw S) | 44.3 | 1216 |
| Diesel (10 ppmw S) | 7.9 | 218 |
| Coke | 5.2 | 142 |
| Torch Oil | 4.6 | 126 |
| Sulphur | 0.1 | 3 |
| Total | 100 | 2749 |

Example 2: Cracking Reaction Products from High-Severity Fluidized Catalytic Cracking of a Gas Condensate Feed In Example 2, the composition of the cracking reaction products resulting from contacting a gas condensate feed with a cracking catalyst under high-severity conditions was determined. The gas condensate feed was a gas condensate produced from the Khuff reservoirs in Saudi Arabia. The HS-FCC process included an AmTech Microdowner reactor system comprising a zeolite cracking catalyst and operated at a reaction temperature of 650° C. and under the same conditions provided in Example 1. Steam was added to the feed upstream of the fluidized cracking reactor. Contact of the gas condensate feed with the cracking catalyst at the reaction conditions produced a cracking reaction product having the composition in Table 3.

TABLE 3

Cracking reaction products from high-severity fluidized catalytic cracking of a gas condensate feed for Example 2

| Feed | Cracking Reaction Product from Gas Condensate Feed | |
| --- | --- | --- |
| Product Yields | wt. % | Ktpa |
| Hydrogen | 0.5 | 13 |
| Methane | 5.1 | 131 |

TABLE 3-continued

Cracking reaction products from high-severity fluidized catalytic cracking of a gas condensate feed for Example 2

| Feed | Cracking Reaction Product from Gas Condensate Feed | |
| --- | --- | --- |
| Product Yields | wt. % | Ktpa |
| Ethylene | 9.5 | 245 |
| Ethane | 3.6 | 93 |
| Propene | 20.2 | 520 |
| Propane | 3.2 | 82 |
| Mixed C4 compounds | 14.4 | 371 |
| Gasoline* | 37.5 | 965 |
| Light Cycle Oil (LCO)** | 2.5 | 64 |
| Heavy Cycle Oil (HCO)*** | 0.8 | 21 |
| Coke | 2.7 | 70 |
| Total | 100 | 2574 |

*C5+ compounds with boiling point temperatures less than 216° C.
**C5+ compounds with boiling point temperatures from 216-343° C.
***C5+ compounds with boiling point temperature of greater than or equal to 343° C.

Example 3: Integrated HS-FCC and Metathesis Process for Naphtha Feed

In Example 3, the conversion of mixed C4 compounds (cracking C4 effluent) of the cracking reaction product from Example 1 to olefins, such as ethylene and propene, through isobutene removal and metathesis of butenes is modeled. AspenPlus® 9 chemical process modeling software (AspenTech) is used to model the isobutene removal and metathesis. The cracking C4 effluent comprising the C4 compounds from the cracking reaction product in Example 1 is introduced to an isobutene removal process. The isobutene removal process includes reaction of the isobutene with methanol in an MTBE reactor to produce methyl tert-butyl ether and separation of the methyl tert-butyl ether from the MTBE reaction products in an MTBE separation system to produce a metathesis feed. For purposes of mathematical modeling, the conversion of isobutene in the MTBE reactor is set to 98.5% conversion and the efficiency of the MTBE separation system for separating methyl tert-butyl ether from the MTBE reaction products is set to 100%.

The metathesis feed is then passed to the metathesis reactor. The metathesis reactor includes a metathesis reaction zone including the metathesis catalyst and a cracking reaction zone including a cracking catalyst and disposed downstream of the metathesis reaction zone, as shown in FIG. 3. The metathesis reactor is modeled using reaction rates representative of experimental reaction rates obtained using metathesis catalyst W-SBA-15 and cracking catalyst MFI-2000 as described in Examples 1, 3, and 6 of U.S. Pat. No. 9,884,794 to Saudi Arabian Oil Company. The simulation is run for 100% efficiency of the metathesis system. In modeling the system for Example 3, the metathesis C5+ effluent and the MTBE effluent are not recycled back to the HS-FCC system. Additionally, the metathesis ethylene effluent is not recycled back to the metathesis system. The metathesis reaction products resulting from high-severity fluidized catalytic cracking, isobutene removal, and metathesis of a naphtha feed are provided in Table 4.

TABLE 4

Metathesis reaction product resulting from high-severity fluidized catalytic cracking, isobutene removal, and metathesis of the naphtha stream

| Stream | Cracking C4 Effluent | Metathesis Feed | Metathesis Reaction Product |
|---|---|---|---|
| Units | ktpa | ktpa | ktpa |
| Fuel Gas | — | — | 1.69 |
| Ethylene | — | — | 24.63 |
| Propene | — | — | 85.19 |
| Propane | — | — | 2.70 |
| Isobutane | 39.85 | 39.85 | 42.37 |
| Normal butane | 26.39 | 26.39 | 27.88 |
| Isobutene | 87.68 | 1.32 | 23.96 |
| 1-Butene | 58.27 | 58.27 | 11.96 |
| Cis-2-Butene | 58.27 | 58.27 | 10.96 |
| Trans-2-Butene | 87.68 | 87.68 | 14.30 |
| Butadiene | 3.57 | 3.57 | 3.57 |
| C5+ | — | — | 26.13 |
| Total | 361.71 | 275.35 | 275.35 |

The removal of isobutene and additional conversion of butenes to ethylene and propene in the metathesis reactor can increase the selectivity and yield of ethylene and propene from the HS-FCC system compared to operating the HS-FCC system by itself, without the metathesis system, when processing a naphtha feed. The following Table 5 compares the product yields of the HS-FCC system by itself against the product yields for the system integrating the HS-FCC system with the isobutene removal unit and metathesis system.

TABLE 5

Comparison of product yields of the HS-FCC system only compared to the product yields of the HS-FCC system integrated with isobutene removal and metathesis for the naphtha feed

| Reaction Product | HS-FCC System Only | | HS-FCC System + Isobutene Removal + Metathesis | | Change |
|---|---|---|---|---|---|
| Yield | wt. % | ktpa | wt. % | ktpa | wt. % |
| Fuel Gas | 3.9 | 107 | 4.0 | 109 | 0.1 |
| Ethylene | 5.1 | 140 | 6.0 | 165 | 0.9 |
| Propene | 14.2 | 390 | 17.3 | 475 | 3.1 |
| Propane | 1.6 | 45 | 1.7 | 47 | — |
| Mixed C4s | 13.2 | 362 | 4.9 | 135 | 8.3 |
| Isobutene | 0.0 | 0 | 3.14 | 86 | 3.1 |
| 95RON (10 ppmwt S) | 44.3 | 1216 | 45.2 | 1242 | 0.9 |
| Diesel (10 ppmwt S) | 7.9 | 218 | 7.9 | 218 | — |
| Coke | 5.2 | 142 | 5.2 | 142 | — |
| Torch Oil | 4.6 | 126 | 4.6 | 126 | — |
| Sulphur | 0.1 | 3 | 0.1 | 3 | — |
| Total | 100.0 | 2749 | 100.0 | 2749 | — |

As shown in Table 5, integrating the HS-FCC system for cracking a naphtha feed with isobutene removal from the cracking C4 effluent and subsequent metathesis of butenes from the C4 effluents reduces the yield of lesser value C4 compounds and increases the yields of more valuable olefins such as ethylene and propene. Integrating the HS-FCC system with an isobutene removal unit and metathesis system may increase the yield of ethylene from the naphtha feed by 17.6% ([change in yield]/[yield from HS-FCC system only]system 100) and may increase the yield of propene from the naphtha feed by 21.8% ([change in yield]/[yield from HS-FCC system only]system 100). Integrating the HS-FCC system with isobutene removal and metathesis decreases the amount of mixed C4 compounds as well as the overall amount of C4 compounds (mixed C4+ isobutene).

Example 4: Integrated HS-FCC and Metathesis Process for Gas Condensate Feed

In Example 4, the conversion of mixed C4 compounds (cracking C4 effluent) of the cracking reaction product from Example 2 (gas condensate feed) to olefins, such as ethylene and propene, through isobutene removal and metathesis of butenes is modeled. AspenPlus 9 chemical process modeling software is used to model the isobutene removal and metathesis. The cracking C4 effluent comprising the C4 compounds from the cracking reaction product in Example 2 is introduced to an isobutene removal system. The isobutene removal system includes reaction of the isobutene with methanol in an MTBE reactor to produce methyl tert-butyl ether and separation of the methyl tert-butyl ether from the MTBE reaction effluent in an MTBE separation system to produce an MTBE-containing effluent and a metathesis feed. For purposes of mathematical modeling the conversion of isobutene in the MTBE reactor is set to 98.5% conversion and the efficiency of the MTBE separation system for separating methyl tert-butyl ether from the MTBE reaction products is set to 100%.

The metathesis feed is then passed from the isobutene removal system to the metathesis reactor. In modeling the system for Example 4, the metathesis C5+ effluent and the MTBE effluent are not recycled back to the HS-FCC system. Additionally, the metathesis ethylene effluent is not recycled back to the metathesis system. The metathesis reaction products resulting from high-severity fluidized catalytic cracking, isobutene removal, and metathesis of a gas condensate feed are provided in Table 6.

TABLE 6

Metathesis reaction product resulting from high-severity fluidized catalytic cracking, isobutene removal, and metathesis of the gas condensate feed

| Stream | Cracking C4 Effluent | Metathesis Feed after Isobutene Removal | Metathesis Reaction Product |
|---|---|---|---|
| Units | ktpa | ktpa | ktpa |
| Methane | — | — | 0.92 |
| Ethane | — | — | 0.42 |
| Ethylene | — | — | 19.95 |
| Propene | — | — | 67.66 |
| Propane | — | — | 2.15 |
| Isobutane | 64.36 | 64.36 | 66.35 |
| Normal butane | 43.76 | 43.76 | 44.95 |
| Isobutene | 95.25 | 1.43 | 19.03 |
| 1-Butene | 56.63 | 56.63 | 9.50 |
| Cis-2-Butene | 46.34 | 46.34 | 8.70 |
| Trans-2-Butene | 59.21 | 59.21 | 11.35 |
| Butadiene | 2.57 | 2.57 | 2.57 |
| C5+ | — | — | 20.75 |
| Total | 368.12 | 274.30 | 274.30 |

For conversion of a gas condensate feed, the removal of isobutene and additional conversion of butenes to ethylene and propene in the metathesis unit can increase the selectivity and yield of ethylene and propene from the HS-FCC system compared to operating the HS-FCC system by itself, without the metathesis system. The following Table 7 compares the product yields from converting a gas condensate feed with the HS-FCC system by itself against the product yields for the system integrating the HS-FCC system with the isobutene removal unit and metathesis system.

TABLE 7

Comparison of product yields of the HS-FCC system only compared to the product yields of the HS-FCC system integrated with isobutene removal and metathesis for the gas condensate feed

| Reaction | HS-FCC System Only | | HS-FCC System + Isobutene Removal + Metathesis | | Change in Yield |
|---|---|---|---|---|---|
| Product Yield | wt. % | ktpa | wt. % | ktpa | wt. % |
| Hydrogen | 0.50 | 13 | 0.5 | 13 | — |
| Methane | 5.10 | 131 | 5.1 | 132 | 0.04 |
| Ethylene | 9.50 | 245 | 10.3 | 265 | 0.79 |
| Ethane | 3.60 | 93 | 3.6 | 93 | — |
| Propene | 20.20 | 520 | 22.9 | 588 | 2.65 |
| Propane | 3.20 | 82 | 3.3 | 85 | 0.09 |
| Mixed C4s | 14.40 | 371 | 6.3 | 162 | −8.08 |
| Isobutene | 0.00 | 0 | 3.6 | 94 | 3.65 |
| Gasoline* | 37.50 | 965 | 38.3 | 986 | 0.84 |
| Light Cycle Oil (LCO)** | 2.50 | 64 | 2.5 | 64 | — |
| Heavy Cycle Oil (HCO)*** | 0.80 | 21 | 0.8 | 21 | — |
| Coke | 2.70 | 70 | 2.7 | 70 | — |
| Total | 100.0 | 2574 | 100.0 | 2572 | — |

*C5+ compounds with boiling point temperatures less than 216° C.
**C5+ compounds with boiling point temperatures from 216-343° C.
***C5+ compounds with boiling point temperature of greater than or equal to 343° C.
Change in yield is calculated as the difference between the yield of the HS-FCC system with butene removal and metathesis and the yield of the HS-FCC system only.

As shown in Table 7, integrating the HS-FCC system for cracking a gas condensate feed with isobutene removal from the cracking C4 effluent and subsequent metathesis of butenes from the C4 effluents reduces the yield of lesser value C4 compounds and increases the yields of greater valuable olefins such as ethylene and propene. Integrating the HS-FCC system with an isobutene removal unit and metathesis system may increase the yield of ethylene from the gas condensate feed by 8.3% ([change in yield]/[yield from HS-FCC system only]system 100) and may increase the yield of propene from the naphtha feed by 13% ([change in yield]/[yield from HS-FCC system only]system 100). Integrating the HS-FCC system with isobutene removal and metathesis may decrease the amount of mixed C4 compounds as well as the overall amount of C4 compounds (mixed C4+ isobutene).

Example 5: Integrated HS-FCC and Metathesis Process Using Naphtha Feed and Ethylene Recycle to the Metathesis Process In Example 5, the effects of recycling the metathesis ethylene effluent back to the metathesis system is investigated. For Example 5, relationships between the ethylene concentration in the metathesis feed to the conversion and selectivity of each constituent of the metathesis effluent have been developed. These relationships were developed by modeling the metathesis system using AspenPlus 9 and using a Gibb's Reactor for the metathesis reactor. Modeling runs of the metathesis system were performed at 560° C. with metathesis feeds comprising concentrations of ethylene in the metathesis feed ranging from 0 wt. % to 30 wt. % and equilibrium proportions of cis-2-butene, trans-2-butene, and isobutene. The conversion of 2-butene (cis-2-butene and trans-2-butene combined) and the selectivity of each constituent of the metathesis reactor effluent were graphed as a function of the mole ratio of ethylene to 2-butene in the metathesis feed. Regression analysis was performed on the data to develop mathematical correlations between the mole ratio of ethylene to 2-butene in the metathesis feed and the 2-butene conversion. Mathematical correlations were also developed for the relationship between the mole ratio of ethylene to 2-butene in the metathesis feed and selectivity of each constituent of the metathesis reactor effluent. The correlations developed for the 2-butene conversion and selectivity of each constituent as a function of the mole ratio of ethylene to 2-butene in the metathesis feed are provided in Table 8.

TABLE 8

Correlations for 2-butene and constituent selectivity as a function of the mole ratio of ethylene to 2-butene in the metathesis feed for a metathesis reaction system.

| Constituent | Correlation |
|---|---|
| 2-Butene Conversion | $0.10106x^2 - 0.13180x + 0.87634$ |
| Propene Selectivity | $-0.04239x^2 + 0.36308x + 0.47604$ |
| Methane Selectivity | $0.00134x^2 + 0.0.00294x + 0.00647$ |
| Ethane Selectivity | $0.00015x^2 + 0.00581x + 0.00298$ |
| Propane Selectivity | $0.00127x^2 + 0.00321x + 0.01510$ |
| Isobutane Selectivity | $0.00173x^2 + 0\ 0.00625x + 0.00833$ |
| n-Butane Selectivity | $0.00125x^2 + 0.00467x + 0.01404$ |
| C5 Selectivity | $0.02615x^2 + 0.04723x + 0.06952$ |
| C6+ Selectivity | $0.02086x^2 + 0.04130x + 0.07650$ |

Where x is equal to the mole ratio of the moles of ethylene to the total moles of 2-butene and 1-butene in the metathesis feed and the 2-butene refers to the combination of cis-2-butene and trans-2-butene.

The mathematical correlations for 2-butene conversion and constituent selectivities as a function of the mole ratio of ethylene to 2-butene in the metathesis feed are used to model the system for producing olefins from the nathpha feed in which system 100% of the metathesis ethylene effluent is recycled back to the metathesis unit. Thus, all of the ethylene produced in the metathesis reaction is passed back to the metathesis system. The modeling of the MTBE system and metathesis system is conducted as described in Example 3 with the addition of the ethylene recycle back to the metathesis reactor. The results of the modeling for Example 5 for a naphtha feed to the system are provided in Table 9.

TABLE 9

Metathesis reaction product resulting from high-severity fluidized catalytic cracking, isobutene removal, and metathesis of the naphtha stream with and without ethylene recycle to the metathesis system

| Stream | Cracking C4 Effluent | HS-FCC System + Isobutene Removal + Metathesis (Ex. 3) | HS-FCC System + Isobutene Removal + Metathesis, with Ethylene Recycle (Ex. 5) |
|---|---|---|---|
| Units | ktpa | ktpa | ktpa |
| Fuel Gas | — | 1.69 | 1.64 |
| Ethylene | — | 24.63 | — |
| Propene | — | 85.19 | 97.97 |
| Propane | — | 2.70 | 2.49 |
| Isobutane | 39.85 | 42.37 | 42.07 |
| Normal butane | 26.39 | 27.88 | 27.58 |
| Isobutene | 87.68 | 23.96 | 29.18 |

TABLE 9-continued

Metathesis reaction product resulting from high-severity fluidized catalytic cracking, isobutene removal, and metathesis of the naphtha stream with and without ethylene recycle to the metathesis system

| Stream | Cracking C4 Effluent | HS-FCC System + Isobutene Removal + Metathesis (Ex. 3) | HS-FCC System + Isobutene Removal + Metathesis, with Ethylene Recycle (Ex. 5) |
|---|---|---|---|
| 1-Butene | 58.27 | 11.96 | 14.56 |
| Cis-2-Butene | 58.27 | 10.96 | 13.34 |
| Trans-2-Butene | 87.68 | 14.30 | 17.41 |
| Butadiene | 3.57 | 3.57 | 3.57 |
| C5+ | — | 26.13 | 25.53 |
| Total | 361.71 | 275.35 | 275.35 |

As shown in Table 9, recycling the ethylene produced in the cross-metathesis of 1-butene and 2-butene back to the metathesis system may increase the yield of propene by 15% from 85.19 ktpa to 97.97 ktpa, when naphtha is used as the hydrocarbon feed to the system for producing olefins. Without being bound by any particular theory, it is believed that the ethylene may undergo cross-metathesis with the 2-butenes in the presence of the metathesis catalyst in the metathesis reactor to produce two propene molecules for every 2-butene molecule. Recycling the metathesis ethylene effluent back to the metathesis system may further increase the selectivity of the metathesis towards greater concentrations of 1-butene, cis-2-butene, trans-2-butene, and isobutene in the metathesis reaction product compared to not recycling the metathesis ethylene effluent. Recycling the metathesis ethylene effluent back to the metathesis system may decrease the yields of propane, isobutane, n-butane, and C5+ compounds in the metathesis reaction product compared to not recycling the metathesis ethylene effluent. It is further noted that the amount of butene produced in the HS-FCC unit when the naphtha stream is used as a feed is sufficient to consume all of the ethylene recycled back to the metathesis reactor. Thus, the yield of ethylene is zero.

Example 6: Integrated HS-FCC and Metathesis Process Using Gas Condensate Feed and Ethylene Recycle to the Metathesis Process The mathematical correlations for 2-butene conversion and constituent selectivities as a function of the mole ratio of ethylene to 2-butene in the metathesis feed determined in Example 5 are again used to model the metathesis unit in the system for producing olefins from a gas condensate feed with 100% of the metathesis ethylene effluent recycled back to the metathesis reactor. Thus, all of the ethylene produced in the metathesis reaction is passed back to the metathesis system. The modeling of the MTBE system and metathesis system is conducted as described in Example 4 with the addition of the ethylene recycle back to the metathesis reactor. The results of the modeling for Example 6 for a gas condensate feed to the system are provided in Table 10.

TABLE 10

Metathesis reaction product resulting from high-severity fluidized catalytic cracking, isobutene removal, and metathesis of the gas condensate feed

| Stream | Cracking C4 Effluent | HS-FCC System + Isobutene Removal + Metathesis (Ex. 3) | HS-FCC System + Isobutene Removal + Metathesis, with Ethylene Recycle (Ex. 5) |
|---|---|---|---|
| Units | ktpa | ktpa | ktpa |
| Methane | — | 0.92 | 0.04 |
| Ethane | — | 0.42 | 0.46 |
| Ethylene | — | 19.95 | 0.79 |
| Propene | — | 67.66 | 78.04 |
| Propane | — | 2.15 | 1.98 |
| Isobutane | 64.36 | 66.35 | 66.11 |
| Normal butane | 43.76 | 44.95 | 44.70 |
| Isobutene | 95.25 | 19.03 | 23.24 |
| 1-Butene | 56.63 | 9.50 | 11.60 |
| Cis-2-Butene | 46.34 | 8.70 | 10.63 |
| Trans-2-Butene | 59.21 | 11.35 | 13.87 |
| Butadiene | 2.57 | 2.57 | 2.57 |
| C5+ | — | 20.75 | 20.27 |
| Total | 368.12 | 274.30 | 274.30 |

As shown in Table 10, recycling the ethylene produced in the cross-metathesis of 1-butene and 2-butene back to the metathesis system can increase the yield of propene by 10.4% from 67.66 ktpa to 78.04 ktpa, when a gas condensate is used as the feed to the system for producing olefins. Without being bound by any particular theory, it is believed that the ethylene may undergo cross-metathesis with the 2-butenes in the presence of the metathesis catalyst in the metathesis reactor to produce two propene molecules for every 2-butene molecule. Recycling the metathesis ethylene effluent back to the metathesis system may further increase the selectivity of the metathesis towards greater concentrations of 1-butene, cis-2-butene, trans-2-butene, and isobutene in the metathesis reaction product compared to not recycling the metathesis ethylene effluent. Recycling the metathesis ethylene effluent back to the metathesis system may decrease the yields of methane, propane, isobutane, n-butane, and C5+ compounds in the metathesis reaction product compared to not recycling the metathesis ethylene effluent. It is noted that when the gas condensate is used as the feed, the ratio of butenes (1-butene and 2-butenes only) to ethylene is less than the ratio of butenes to ethylene resulting from using the naphtha feed (Example 5). Thus, in Example 6 (gas condensate), the amount of butane is not enough to consume all of the ethylene recycled back to the metathesis reactor, which results in a positive yield of ethylene from the process simulated in Example 6.

In a first aspect of the present disclosure, a process for producing olefins includes contacting a hydrocarbon feed with a cracking catalyst under high-severity conditions to produce a cracking reaction effluent comprising at least butenes. The high-severity conditions may comprise a temperature of greater than or equal to 500° C., a residence time of less than 3 seconds, and a cracking catalyst to hydrocarbon weight ratio of greater than 5:1. The process may further include contacting at least a portion of the cracking reaction effluent with a metathesis catalyst, where the contacting may cause metathesis of at least a portion of the butenes in the portion of the cracking reaction effluent to produce a metathesis reaction product. The process may further include separating the metathesis reaction product into a metathesis C5+ effluent and at least one olefin-containing effluent. The olefin-containing effluent may include at least one of ethylene, propene, butenes, or combinations of these. The process may further include contacting the metathesis C5+ effluent with the cracking catalyst and the hydrocarbon feed under high-severity conditions to produce the cracking reaction effluent.

A second aspect of the present disclosure may include the first aspect, in which the hydrocarbon feed may include a naphtha, a gas condensate, or both.

A third aspect of the present disclosure may include any one of the first through second aspects, in which the cracking reaction effluent may comprise isobutene and the process may further include removing isobutene from at least a portion of the cracking reaction effluent to produce a metathesis feed.

A fourth aspect of the present disclosure may include the third aspect, in which removing isobutene may include contacting the at least a portion of the cracking reaction effluent with methanol under reaction conditions sufficient to convert at least a portion of the isobutene in the portion of the cracking reaction effluent to methyl tert-butyl ether to produce an MTBE reactor effluent comprising the methyl tert-butyl ether. Removing isobutene may further include separating the MTBE reactor effluent into at least an MTBE-containing effluent comprising the methyl tert-butyl ether and a metathesis feed comprising butene.

A fifth aspect of the present disclosure may include the fourth aspect, further comprising contacting the MTBE-containing effluent with the cracking catalyst under high-severity conditions, where the contacting may cause at least a portion of the methyl tert-butyl ether in the MTBE-containing effluent to undergo catalytic cracking reactions to produce at least a portion of the cracking reaction effluent.

A sixth aspect of the present disclosure may include any one of the first through fifth aspects, comprising contacting at least a portion of the cracking reaction effluent with the metathesis catalyst and a cracking downstream of the metathesis catalyst, where the contacting with the cracking catalyst may cause at least a portion of C5+ olefins produced through metathesis to undergo cracking reactions to produce additional propene, ethylene, or both.

A seventh aspect of the present disclosure may include any one of the first through sixth aspects, comprising separating the metathesis reaction product into the metathesis C5+ effluent, a metathesis C4 effluent, a metathesis propene effluent, and a metathesis ethylene effluent.

An eighth aspect of the present disclosure may include the seventh aspect, further comprising, after separating the metathesis reaction product, passing at least a portion of the metathesis C4 effluent back into contact with the metathesis catalyst, where contacting the metathesis C4 effluent with the metathesis catalyst may cause further metathesis of at least a portion of the butenes in the metathesis C4 effluent to produce the metathesis reaction product.

A ninth aspect of the present disclosure may include any one of the seventh or eighth aspects, further comprising passing at least a portion of the metathesis ethylene effluent back into contact with the metathesis catalyst.

A tenth aspect of the present disclosure may include any one of the seventh or eighth aspects, where the metathesis ethylene effluent is not passed back into contact with the metathesis catalyst and no supplemental ethylene is introduced into contact with the metathesis catalyst.

An eleventh aspect of the present disclosure may include any one of the first through tenth aspects, further comprising separating the cracking reaction effluent into a cracking C4 effluent and at least one other effluent stream, where the cracking C4 effluent comprises butene.

A twelfth aspect of the present disclosure may include any one of the first through eleventh aspects, comprising contacting the hydrocarbon feed with the cracking catalyst at a temperature of from 500° C. to 800° C., for a residence time of from 0.2 seconds to 3 seconds, and at a cracking catalyst to hydrocarbon weight ratio of from 5:1 to 40:1.

A thirteenth aspect of the present disclosure may include a process for producing olefins, the process including introducing a hydrocarbon feed to a high-severity fluidized catalytic cracking system and contacting the hydrocarbon feed with a cracking catalyst under high-severity conditions in the high-severity fluidized catalytic cracking system to produce a cracking reaction effluent comprising butene. The high-severity conditions may include a temperature of greater than or equal to 500° C., a residence time of less than or equal to 3 seconds, and a weight ratio of the cracking catalyst to hydrocarbon of 5:1. The process may further include passing at least a portion of the cracking reaction effluent to a metathesis system. The at least a portion of the cracking reaction effluent may include a cracking C4 effluent that includes at least butene. The process may further include contacting the cracking C4 effluent with a metathesis catalyst in the metathesis system, where the contacting may cause at least a portion of the butene in the cracking C4 effluent to undergo a metathesis reaction to produce a metathesis reaction effluent comprising at least one of ethylene, propene, or both. The process may further include separating a metathesis C5+ effluent from the metathesis reaction effluent and passing the metathesis C5+ effluent back to the high-severity fluidized catalytic cracking unit.

A fourteenth aspect of the present disclosure may include the thirteenth aspect, in which the hydrocarbon feed may include a naphtha stream, a gas condensate stream, or both.

A fifteenth aspect of the present disclosure may include any one of the thirteenth or fourteenth aspects, in which the cracking C4 effluent may include isobutene and the process may further comprise passing at least a portion of the cracking C4 effluent to an isobutene removal unit.

A sixteenth aspect of the present disclosure may include the fifteenth aspect, further comprising contacting the portion of the cracking C4 effluent with methanol in an MTBE reactor of the isobutene removal unit under reaction conditions sufficient to convert at least a portion of the isobutene in the cracking C4 effluent to methyl tert-butyl ether to produce an MTBE reactor effluent and separating the MTBE reactor effluent into at least an MTBE-containing effluent and a metathesis feed. The metathesis feed may comprise butene, and the process may further include passing the metathesis feed to the metathesis system.

A seventeenth aspect of the present disclosure may include the sixteenth aspect, further comprising passing at least a portion of the MTBE-containing effluent back to the high-severity fluidized catalytic cracking system.

An eighteenth aspect of the present disclosure may include any one of the thirteenth through seventeenth aspects, in which the metathesis system may comprise a metathesis reaction zone comprising the metathesis catalyst and a cracking reaction zone comprising a cracking catalyst, where the cracking reaction zone is directly downstream of the metathesis reaction zone.

A nineteenth aspect of the present disclosure may include the eighteenth aspect, comprising passing at least a portion of the cracking C4 effluent through the metathesis reaction zone and the cracking reaction zone downstream of the metathesis reaction zone. Contact the butene in the cracking C4 effluent with the metathesis catalyst in the metathesis reaction zone may cause at least a portion of the butene in the cracking C4 effluent to undergo a metathesis reaction to produce at least propylene and C5+ olefins. Contacting the C5+ olefins with the cracking catalyst in the cracking reaction zone may cause at least a portion of the C5+ olefins to undergo catalytic cracking to produce at least one of ethylene, propylene, or both.

A twentieth aspect of the present disclosure may include any one of the thirteenth through nineteenth aspects, comprising separating the metathesis reaction effluent into a metathesis ethylene effluent, a metathesis propene effluent, a metathesis C4 effluent, and the metathesis C5+ effluent.

A twenty-first aspect of the present disclosure may include the twentieth aspect, further comprising passing at least a portion of the metathesis C4 effluent back to the metathesis system or to an isobutene removal unit upstream of the metathesis system.

A twenty-second aspect of the present disclosure may include any one of the twentieth or twenty-first aspects, further comprising passing at least a portion of the metathesis ethylene effluent back to the metathesis system or to an isobutene removal unit upstream of the metathesis system.

A twenty-third aspect of the present disclosure may include the twenty-second aspect, in which the metathesis system may include a metathesis reactor comprising a metathesis reaction zone having the metathesis catalyst and a cracking reaction zone downstream of the metathesis reaction zone and having a cracking catalyst. The metathesis system may further include a supplemental metathesis reactor comprising a metathesis reaction zone, where the supplemental metathesis reactor may be operated in parallel with the metathesis reactor. The portion of the metathesis ethylene effluent may be passed to the supplemental metathesis reactor.

A twenty-fourth aspect of the present disclosure may include any one of the thirteenth through twenty-first aspects, where no portion of the metathesis ethylene effluent is passed to the metathesis system and no supplemental ethylene is introduced to the metathesis system.

A twenty-fifth aspect of the present disclosure may include any one of the thirteenth through twenty-fourth aspects, further comprising separating the cracking reaction effluent into the cracking C4 effluent comprising butene, and at least one of a cracking propene effluent, a cracking ethylene effluent, or a greater boiling temperature effluent.

A twenty-sixth aspect of the present disclosure may include the twenty-fifth aspect, in which separating the cracking reaction effluent may comprise passing the cracking reaction effluent to a cracking effluent separation system comprising one or a plurality of separators operable to separate the cracking reaction effluent into the cracking C4 effluent and at least one of a cracking propene effluent, a cracking ethylene effluent, a lesser-molecular weight gas effluent, greater boiling temperature effluent, or combinations of these.

A twenty-seventh aspect of the present disclosure may include any one of the thirteenth through twenty-sixth aspects, comprising contacting the hydrocarbon feed with the cracking catalyst at a temperature of from 500° C. to 800° C., for a residence time of from 0.2 seconds to 3 seconds, and at a cracking catalyst to hydrocarbon weight ratio of from 5:1 to 40:1.

A twenty-eighth aspect of the present disclosure may include a system for producing olefins. The system may include a high-severity fluidized catalytic cracking system comprising a cracking catalyst and operable to contact a hydrocarbon feed with the cracking catalyst under high-severity conditions comprising a temperature of greater than or equal to 500° C., a residence time of less than or equal to 3 seconds, and a weight ratio of cracking catalyst to hydrocarbon of greater than or equal to 5:1 to produce a cracking reaction effluent comprising ethylene, propene, butene, or combinations of these. The system for producing olefins may further include an isobutene removal unit downstream of the high-severity fluidized catalytic cracking system. The isobutene removal unit may be operable to receive a cracking C4 effluent from the high-severity fluidized catalytic cracking system and remove at least a portion of the isobutene from the cracking C4 effluent to produce a metathesis feed having a decreased concentration of isobutene compared to the cracking C4 effluent. The system may further include a metathesis system downstream of the isobutene removal unit. The metathesis system may be operable to contact the metathesis feed with at least a metathesis catalyst to produce a metathesis reaction effluent comprising at least propene, ethylene, or both. The system may further include a C5+ recycle extending from a C5+ outlet of the metathesis system to an inlet of the high-severity fluidized catalytic cracking system, the C5+ recycle operable to pass a metathesis C5+ effluent from the metathesis system back to the high-severity fluidized catalytic cracking system.

A twenty-ninth aspect of the present disclosure may include the twenty-eighth aspect, in which the isobutene removal unit may comprise an MTBE reactor operable to convert at least a portion of the isobutene in the cracking C4 effluent to methyl tert-butyl ether.

A thirtieth aspect of the present disclosure may include the twenty-ninth aspect, in which the isobutene removal unit comprises an MTBE separation system operable to separate an MTBE reactor effluent from the MTBE reactor into at least an MTBE-containing effluent and the metathesis feed.

A thirty-first aspect of the present disclosure may include the thirtieth aspect, further comprising an MTBE recycle loop fluidly coupled to an MTBE-containing effluent outlet of the isobutene removal unit and an inlet of the high-severity fluidized catalytic cracking system. The MTBE recycle loop may be operable to recycle at least a portion of the MTBE-containing effluent from the isobutene removal unit back to the inlet of the high-severity fluidized catalytic cracking system.

A thirty-second aspect of the present disclosure may include any one of the twenty-eighth through thirty-first aspects, in which the high-severity fluidized catalytic cracking system comprises a cracking effluent separation system comprising one or a plurality of separators that may be operable to separate the cracking reaction effluent into the cracking C4 effluent and at least one other cracking effluent.

A thirty-third aspect of the present disclosure may include the thirty-second aspect, in which the at least one other cracking effluent may include at least one of a cracking ethylene effluent, a cracking propene effluent, a greater boiling temperature effluent, or combinations of these.

A thirty-fourth aspect of the present disclosure may include any one of the twenty-eighth through thirty-third aspects, in which the metathesis system comprises a metathesis reactor and a metathesis separation system downstream of the metathesis reactor, the metathesis separation system comprising one or a plurality of separators operable to separate the metathesis reaction product into one or more of a metathesis ethylene effluent, a metathesis propene effluent, a metathesis C4 effluent, a metathesis C5+ effluent, or combinations of these.

A thirty-fifth aspect of the present disclosure may include any one of the twenty-eighth through thirty-fourth aspects, in which the metathesis system comprises a metathesis reactor that includes a metathesis reaction zone comprising a metathesis catalyst and a cracking reaction zone comprising a cracking catalyst, where the cracking reaction zone is directly downstream of the metathesis reaction zone.

A thirty-sixth aspect of the present disclosure may include the thirty-fifth aspect, in which the metathesis system may further comprise a supplemental metathesis reactor comprising a supplemental metathesis catalyst, where the supplemental metathesis reactor is operated in parallel with the metathesis reactor.

A thirty-seventh aspect of the present disclosure may include the thirty-sixth aspect, further comprising a metathesis ethylene recycle that may be operable to pass at least a portion of a metathesis ethylene effluent from a metathesis separation system to the supplemental metathesis reactor.

A thirty-eighth aspect of the present disclosure may include any one of the twenty-eighth through thirty-seventh aspects, further comprising a combined separation system operable to receive the cracking reaction effluent and the metathesis reaction effluent and separate the cracking reaction effluent and the metathesis reaction effluent into at least a C4 effluent, an ethylene effluent, and a propene effluent.

It should now be understood that various aspects of the systems and processes for producing olefins that include high-severity fluidized catalytic cracking integrated with metathesis are described and such aspects may be utilized in conjunction with various other aspects.

Throughout this disclosure ranges are provided for various processing parameters and operating conditions for the systems and processes for producing olefins and the compositions of various streams and mixtures. It will be appreciated that when one or more explicit ranges are provided the individual values and the sub-ranges formed within the range are also intended to be provided as providing an explicit listing of all possible combinations is prohibitive. For example, a provided range of 1-10 also includes the individual values, such as 1, 2, 3, 4.2, and 6.8, as well as all the ranges that may be formed within the provided bounds, such as 1-8, 2-4, 6-9, and 1.3-5.6.

It is noted that recitations herein of "at least one" component, element, etc., should not be used to create an inference that the alternative use of the articles "a" or "an" should be limited to a single component, element, etc.

It should be apparent to those skilled in the art that various modifications and variations can be made to the described embodiments without departing from the spirit and scope of the claimed subject matter. Thus, it is intended that the specification cover the modifications and variations of the various described embodiments provided such modifications and variations come within the scope of the appended claims and their equivalents.

What is claimed is:

1. A process for producing olefins, the process comprising:
   contacting a hydrocarbon feed with a cracking catalyst under high-severity conditions in a high-severity fluidized catalytic cracking system to produce a cracking reaction effluent comprising at least butenes, wherein the butenes comprises normal butenes and isobutene, where the high-severity conditions comprise a temperature of greater than or equal to 500° C.;
   contacting a portion of the cracking reaction effluent with methanol in an MTBE reactor of an isobutene removal unit under reaction conditions sufficient to convert at least a portion of the isobutene in the portion of the cracking reaction effluent to methyl tert-butyl ether to produce an MTBE reactor effluent;
   separating the MTBE reactor effluent into at least an MTBE-containing effluent and a metathesis feed, the metathesis feed comprising butene;
   contacting the metathesis feed with a metathesis catalyst, where the contacting causes metathesis of at least a portion of the butenes in the metathesis feed to produce a metathesis reaction product comprising at least one of ethylene, propene, butenes, or combinations thereof; and
   passing at least a portion of the MTBE-containing effluent back to the high-severity fluidized catalytic cracking system.

2. The process of claim 1, in which the hydrocarbon feed comprises a naphtha, a gas condensate, or both.

3. The process of claim 1, comprising:
   separating the metathesis reaction product into a metathesis C5+ effluent, a metathesis C4 effluent, a metathesis propene effluent, and a metathesis ethylene effluent; and
   after separating the metathesis reaction product, passing at least a portion of the metathesis C4 effluent back into contact with the metathesis catalyst, where contacting the metathesis C4 effluent with the metathesis catalyst causes further metathesis of at least a portion of the butenes in the metathesis C4 effluent to produce the metathesis reaction product.

4. The process of claim 3, further comprising passing at least a portion of the metathesis ethylene effluent back into contact with the metathesis catalyst.

5. The process of claim 1, further comprising separating the cracking reaction effluent into a cracking C4 effluent and at least one other effluent stream, where the cracking C4 effluent comprises the at least butenes, and the cracking C4 effluent is the portion of the cracking effluent contacted with methanol in the MTBE reactor.

6. The process of claim 1, comprising separating the metathesis reaction effluent into a metathesis ethylene effluent, a metathesis propene effluent, a metathesis C4 effluent, and the metathesis C5+ effluent, and passing at least a portion of the metathesis C4 effluent back to the metathesis system or to the isobutene removal unit upstream of the metathesis system.

7. The process of claim 6, comprising passing at least a portion of the metathesis C4 effluent back to the metathesis system and contacting the at least a portion of the metathesis C4 effluent with the metathesis catalyst, where contacting the at least a portion of the metathesis C4 effluent with the metathesis catalyst causes further metathesis of the butenes in the at least a portion of the metathesis C4 effluent to produce the metathesis reaction product.

8. The process of claim 6, further comprising passing at least a portion of the metathesis ethylene effluent back to the metathesis system.

9. A process for producing olefins, the process comprising:
   introducing a hydrocarbon feed to a high-severity fluidized catalytic cracking system;
   contacting the hydrocarbon feed with a cracking catalyst under high-severity conditions in the high-severity fluidized catalytic cracking system to produce a cracking reaction effluent comprising butenes, wherein the butenes comprise normal butenes and isobutene, where the high-severity conditions comprise a temperature of greater than or equal to 500° C., a residence time of less than or equal to 3 seconds, and a weight ratio of the cracking catalyst to hydrocarbon of 5:1;

contacting a portion of the cracking reaction effluent with methanol in an MTBE reactor of an isobutene removal unit under reaction conditions sufficient to convert at least a portion of the isobutene in the portion of the cracking reaction effluent to methyl tert-butyl ether to produce an MTBE reactor effluent;

separating the MTBE reactor effluent into at least an MTBE-containing effluent and a metathesis feed;

passing the metathesis feed to a metathesis system, the at least a portion of the cracking reaction effluent comprising a cracking C4 effluent that includes at least butene;

contacting the metathesis feed with a metathesis catalyst in the metathesis system, where the contacting causes at least a portion of the butenes in the metathesis feed to undergo a metathesis reaction to produce a metathesis reaction effluent comprising at least one of ethylene, propene, or both; and passing at least a portion of the MTBE-containing effluent back to the high-severity fluidized catalytic cracking system.

10. The process of claim 9, in which the hydrocarbon feed comprises a naphtha, a gas condensate, or both.

11. The process of claim 9, further comprising separating the cracking reaction effluent into a cracking C4 effluent and at least one other effluent stream, where the cracking C4 effluent comprises the butenes, and the cracking C4 effluent is the portion of the cracking reaction effluent contacted with methanol in the MTBE reactor.

12. A process for producing olefins, the process comprising:

contacting a hydrocarbon feed with a cracking catalyst under high-severity conditions to produce a cracking reaction effluent comprising at least butenes, where the high-severity conditions comprise a temperature of greater than or equal to 500° C., a residence time of less than 3 seconds, and a cracking catalyst to hydrocarbon weight ratio of greater than 5:1;

contacting at least a portion of the cracking reaction effluent with a metathesis catalyst, where the contacting causes metathesis of at least a portion of the butenes in the portion of the cracking reaction effluent to produce a metathesis reaction product;

separating the metathesis reaction product into a metathesis C5+ effluent and at least one olefin-containing effluent, the olefin-containing effluent comprising at least one of ethylene, propene, butenes, or combinations thereof;

contacting the metathesis C5+ effluent with the cracking catalyst and the hydrocarbon feed under high-severity conditions to produce the cracking reaction effluent, in which the cracking reaction effluent further comprises isobutene and the process further comprises removing isobutene from at least a portion of the cracking reaction effluent to produce a metathesis feed, in which removing isobutene comprises:
contacting the at least a portion of the cracking reaction effluent with methanol under reaction conditions sufficient to convert at least a portion of the isobutene in the portion of the cracking reaction effluent to methyl tert-butyl ether to produce an MTBE reactor effluent comprising the methyl tert-butyl ether; and separating the MTBE reactor effluent into at least an MTBE-containing effluent comprising the methyl tert-butyl ether and a metathesis feed comprising butene, where the metathesis feed is the at least a portion of the cracking reaction effluent contacted with the metathesis catalyst, and in which, the process further comprises contacting the MTBE-containing effluent with the cracking catalyst under high-severity conditions, where the contacting causes at least a portion of the methyl tert-butyl ether in the MTBE-containing effluent to undergo catalytic cracking reactions to produce at least a portion of the cracking reaction effluent.

13. The process of claim 12, in which the hydrocarbon feed comprises a naphtha, a gas condensate, or both.

14. The process of claim 12, comprising:

separating the metathesis reaction product into the metathesis C5+ effluent, a metathesis C4 effluent, a metathesis propene effluent, and a metathesis ethylene effluent; and after separating the metathesis reaction product, passing at least a portion of the metathesis C4 effluent back into contact with the metathesis catalyst, where contacting the metathesis C4 effluent with the metathesis catalyst causes further metathesis of at least a portion of the butenes in the metathesis C4 effluent to produce the metathesis reaction product.

15. The process of claim 14, further comprising passing at least a portion of the metathesis ethylene effluent back into contact with the metathesis catalyst.

16. The process of claim 12, further comprising separating the cracking reaction effluent into a cracking C4 effluent and at least one other effluent stream, where the cracking C4 effluent comprises the butenes and isobutene, and the cracking C4 effluent is the at least a portion of the cracking reaction effluent contacted with methanol.

\* \* \* \* \*